United States Patent [19]
Park et al.

[11] Patent Number: 5,789,601
[45] Date of Patent: Aug. 4, 1998

[54] METHOD OF INACTIVATION OF VIRAL AND BACTERIAL BLOOD CONTAMINANTS

[75] Inventors: Sang Chul Park, Arcadia; Raymond P. Goodrich, Jr.; Nagender Yerram, both of Pasadena; Samuel O. Sowemimo-Coker, Arcadia, all of Calif.; Matthew S. Platz, Columbus; Brian M. Aquila, Padresville, both of Ohio

[73] Assignee: Baxter International Inc., Deerfield, Ill.

[21] Appl. No.: 427,080

[22] Filed: Apr. 21, 1995

Related U.S. Application Data

[60] Division of Ser. No. 311,125, Sep. 22, 1994, Pat. No. 5,516,629, and a continuation-in-part of Ser. No. 91,674, Jul. 13, 1993, Pat. No. 5,418,130, which is a continuation-in-part of Ser. No. 47,749, Apr. 14, 1993, said Ser. No. 311,125, is a continuation-in-part of Ser. No. 165,305, Dec. 10, 1993, Pat. No. 5,587,490, which is a continuation-in-part of Ser. No. 47,749, Apr. 14, 1993, which is a continuation-in-part of Ser. No. 685,931, Apr. 16, 1991, abandoned, which is a continuation-in-part of Ser. No. 656,254, Feb. 15, 1991, abandoned, Ser. No. 632,277, Dec. 20, 1990, abandoned, and Ser. No. 510,234, Apr. 16, 1990, abandoned.

[51] Int. Cl.⁶ .................. C07D 311/08; C07D 311/12; C07D 311/14
[52] U.S. Cl. .................................. 549/283; 549/285
[58] Field of Search ........................ 549/283, 285

[56] References Cited

U.S. PATENT DOCUMENTS

| | | | |
|---|---|---|---|
| 4,296,039 | 10/1981 | Della Valle | 260/343.45 |
| 4,362,741 | 12/1982 | Della Valle | 424/281 |
| 4,613,322 | 9/1986 | Edelson | 604/6 |
| 4,748,120 | 5/1988 | Wiesehahn | 435/173 |
| 4,878,891 | 11/1989 | Judy et al. | 604/5 |
| 4,889,129 | 12/1989 | Dougherty et al. | 128/664 |
| 5,176,921 | 1/1993 | Weisehahn | 424/529 |

FOREIGN PATENT DOCUMENTS

WO 94/14956  7/1994  WIPO.

OTHER PUBLICATIONS

Goodrich et al. (1994) Proc. Natl. Acad. Sci. USA 91; pp. 5552–556.

Kunicki et al. (1975) Transfusion 15(5), pp. 414–421.

Midden, W.R. (1988) *Psoralen DNA Photobiology* vol. II (ed. F.P. Gasparro, Ph.D.) CRC Press, Chapter 4, pp. 1–49.

Sethna and Shah (1945) Chem. Rev. 36, pp. 1–62.

Sethna and Phadke (1953) Organic Reactions 7, pp. 1–58.

Rodighiero *Psoralen DNA Photobiol*, Chap. 2, "New Psoralen and Angelicin Derivatives", CRC Press 1:37–104, 1990.

Fukunga, et al., Production of Frameshift Mutations in Salmonella by Phenanthridinium Derivatives: Enzymatic Activation and Photoaffinity Labeling. (1984), Mutation Research, 127:31–37.

*Primary Examiner*—Ba K. Trinh
*Attorney, Agent, or Firm*—Barry J. Swanson; Denis M. Serewicz; Bradford R. L. Price

[57] ABSTRACT

Viral and bacterial contaminants present in biological solutions are inactivated by mixing one of a novel class of photosensitizer with said solution and irradiating the mixture.

11 Claims, 13 Drawing Sheets

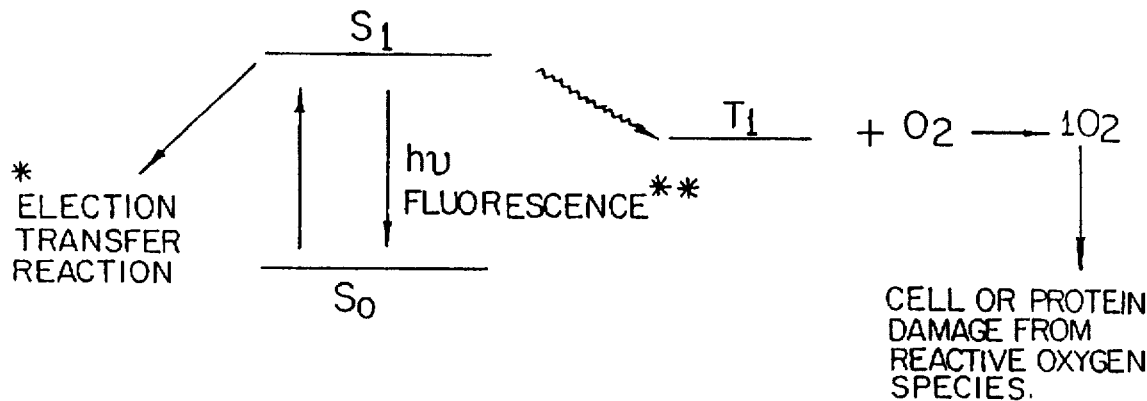

* THE ELECTRON TRANSFER REACTION PROCEEDS AS A FUNCTION OF DISTANCE OF SEPARATION BETWEEN DONOR AND ACCEPTOR. IN NUCLEIC ACIDS, GUANINE RESIDUES SERVE AS THE PRINCIPAL DONORS.

** THE FLUORESCENCE PATHWAY SERVES AS A MEANS FOR EXPENDING ENERGY IN A WAY THAT IS NOT DETRIMENTAL. LESS $^1O_2$ IS PRODUCED BY A MOLECULE THAT CAN FLUORESCE THAN IN A MOLECULE THAT EFFICIENTLY FORMS EXCITED TRIPLET STATES.

$S_0$ = GROUND STATE
$S_1$ = EXCITED SINGLET STATE
$T_1$ = EXCITED TRIPLET STATE
$^1O_2$ = SINGLET OXYGEN

FIG. 1

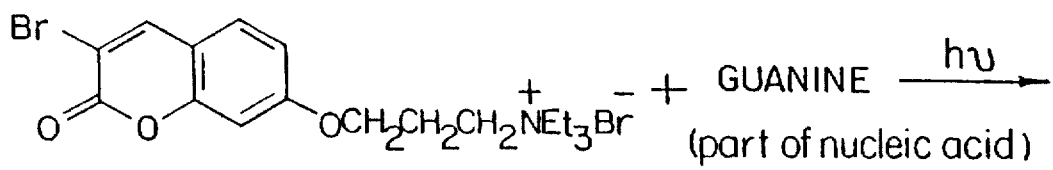
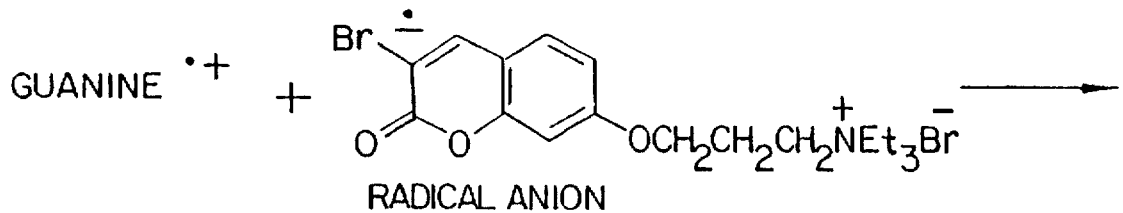
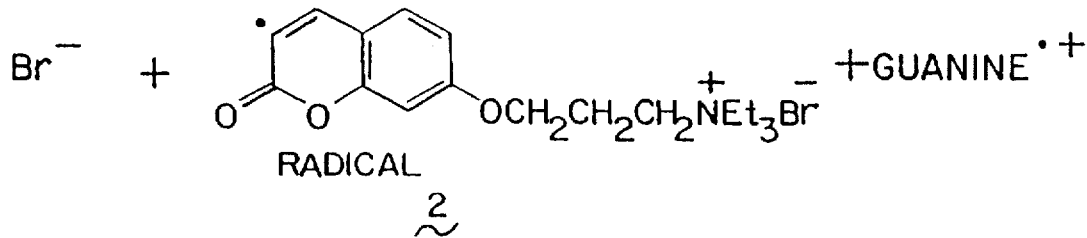
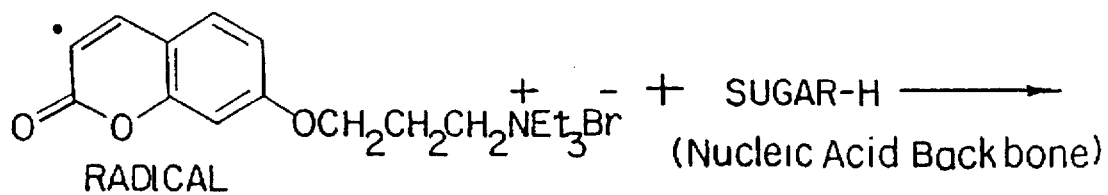
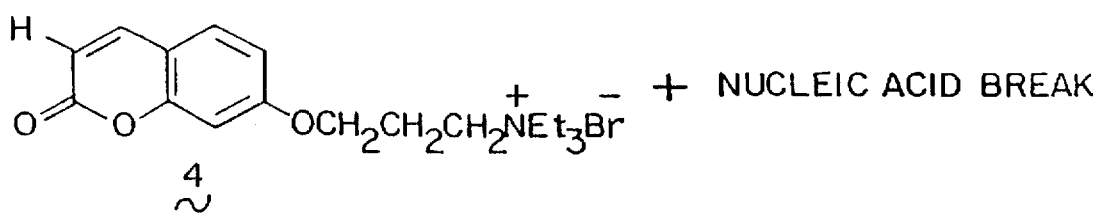
FIG. 2

METHOD OF INACTIVATION OF VIRAL AND BACTERIAL BLOOD CONTAMINANTS

RELATED APPLICATIONS

This application is a divisional of Ser. No. 08/311,125 filed Sep. 22, 1994, now issued as U.S. Pat. No. 5,516,629 which is a continuation-in-part of Ser. No. 08/165,305 filed Dec. 10, 1993, now U.S. Pat. No. 5,587,490 which is a continuation-in-part of Ser. No. 08/047,749 filed Apr. 14, 1993 pending, which is a continuation-in-part of Ser. No. 07/685,931, filed Apr. 16, 1991, now abandoned which is a continuation-in-part of Ser. No. 07/656,254, filed Feb. 15, 1991, now abandoned and a continuation-in-part of Ser. No. 07/632,277, now abandoned filed Dec. 20, 1990, and a continuation-in-part of Ser. No. 07/510,234, filed Apr. 16, 1990, now abandoned. This is also a continuation-in-part of Ser. No. 08/091,674 filed Jul. 13, 1993 now issued as U.S. Pat. No. 5,418,130 which is also a continuation-in-part of Ser. No. 08/047,749 filed Apr. 14, 1993, pending. All of these applications are incorporated by reference herein in their entirety.

FIELD OF THE INVENTION

This invention relates to the general field of the inactivation of viral and bacterial contamination of blood and blood products including compositions comprising peripheral blood cells (red blood cells, platelets, leukocytes, stem cells, etc.), plasma protein fractions (albumin, clotting factors, etc.) from collected whole blood, the blood of virally infected persons, ex vivo media used in the preparation of anti-viral vaccines, and cell culture media such as fetal bovine serum, bovine serum or products derived from these sources.

BACKGROUND OF THE INVENTION

A major concern in the transfusion of donated, stored whole human blood or the various blood cells or protein fractions isolated from whole blood is the possibility of viral contamination. Of particular concern are the blood-borne viruses that cause hepatitis (especially hepatitis A, hepatitis B, and hepatitis C) and acquired immune deficiency syndrome (AIDS). While any number of cell washing protocols may reduce the viral contamination load for samples of blood cells, by physical elution of the much smaller virus particles, such washing alone is insufficient to reduce viral contamination to safe levels. In fact, some viruses are believed to be cell-associated, and unlikely to be removed by extensive washing and centrifugal pelleting of the cells. Current theory suggests that safe levels will ultimately require at least a 6 log (6 orders of magnitude) demonstrated reduction in infectious viral titer for cellular blood components. This 6 log threshold may be greater for plasma protein components, especially the clotting factors (Factor VIII, Factor IX) that are administered throughout the life of some hemophilia patients.

All blood collected in the United States is now screened for six infectious agents: HIV-1, HIV-2, HTLV-1, hepatitis B virus, hepatitis C virus and syphilis. Additionally, donors are screened for risk factors, and potential donors are eliminated that are considered at risk for the HIV virus. Despite these measures, the risk of becoming infected by a potentially deadly virus or bacteria via the transfusion of blood or blood products remains serious. Screens for contaminants are by nature not foolproof. There is also the quite likely occurrence of new infectious agents that enter the blood supply before the significance of the event is known. For example, by the end of June 1992, the Center for Disease Control reports that 4,959 AIDS cases could be traced to the receipt of blood transfusions, blood components or tissue.

Viral inactivation by stringent sterilization is not acceptable since this could also destroy the functional components of the blood, particularly the erythrocytes (red blood cells) and thrombocytes (platelets) and the labile plasma proteins, such as clotting factor VIII. Viable RBC's can be characterized by one or more of the following: capability of synthesizing ATP; cell morphology; $P_{50}$ values; filterability or deformability; oxyhemoglobin, methemoglobin and hemochrome values; MCV, MCH, and MCHC values; cell enzyme activity; and in vivo survival. Thus, if virally inactivated cells are damaged to the extent that the cells are not capable of metabolizing or synthesizing ATP, or the cell circulation is compromised, then their utility in transfusion medicine is compromised.

Viral inactivation by stringent steam sterilization is not acceptable since this also destroys the functional components of the blood, particularly the blood cells and plasma proteins. Dry heat sterilization, like wet steam, is harmful to blood cells and blood proteins at the levels needed to reduce viral infectivity. Use of stabilizing agents such as carbohydrates does not provide sufficient protection to the delicate blood cells and proteins from the general effects of exposure to high temperature and pressure.

Methods that are currently employed with purified plasma protein fractions, often followed by lyophilization of the protein preparation, include treatment with organic solvents and heat or extraction with detergents to disrupt the lipid coat of membrane enveloped viruses. Lyophilization (freeze-drying) alone has not proven sufficient to inactivate viruses, or to render blood proteins sufficiently stable to the effects of heat sterilization. The organic solvent or detergent method employed with purified blood proteins cannot be used with blood cells as these chemicals destroy the lipid membrane that surrounds the cells.

Another viral inactivation approach for plasma proteins first demonstrated in 1958 has involved the use of a chemical compound, beta-propiolactone, with ultraviolet (U.V.) irradiation. This method has not found acceptance in the United States due to concern over the toxicity of beta-propiolactone in the amounts used to achieve some demonstrable viral inactivation and also due to unacceptable levels of damage to the proteins caused by the chemical agents. Concern has also been raised over the explosive potential for beta-propiolactone as well.

There is significant interest in an effective viral inactivation treatment for human blood components, which will not damage the valuable blood cells or proteins. The treatment must be nontoxic and selective for viruses, while allowing the intermingled blood cells or proteins to survive unharmed.

There is an immediate need to develop protocols for the inactivation of viruses that can be present in the human red blood cell supply. For example, only recently has a test been developed for Non A, Non B hepatitis, but such screening methods, while reducing the incidence of viral transmission, do not make the blood supply completely safe or virus free. Current statistics indicate that the transfusion risk per unit of transfused blood is as high as 1:3,000 for Non A, Non B hepatitis (hepatitis C), and ranges from 1:60,000 to 1:225,000 for HIV, depending on geographic location. Clearly, it is desirable to develop a method which inactivates or removes virus indiscriminately from the blood.

Contamination problems also exist for blood plasma protein fractions, such as plasma fractions containing immune globulins and clotting factors. For example, new cases of non A, non B hepatitis and hepatitis A have occurred in hemophilia patients receiving protein fractions containing Factor VIII which have been treated for viral inactivation according to approved methods. Therefore, there is a need for improved viral inactivation treatment of blood protein fractions.

The crosslinking reaction is specific for a thymine (DNA) or uracil (RNA) base and will proceed only if the psoralen is intercalated in a site containing thymine or uracil. The initial photoadduct can absorb a second UVA photon and react with a second thymine or uracil on the opposing strand of the double helix to crosslink the two strands of the double helix.

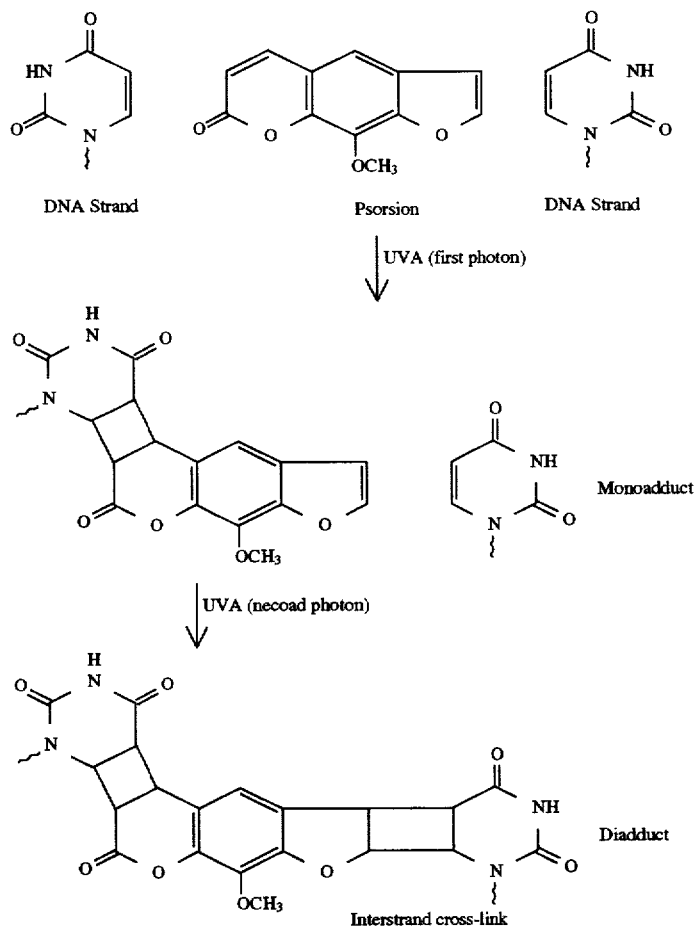

The ability to inactivate bacterial contaminants from blood and blood products may be as critical as reducing viral contaminants. Between 1986 and 1991, the Food and Drug Administration reported that 15.9% of all transfusion related fatalities were associated with the transfusion of bacterially contaminated blood components. Most of these fatalities were due to the transfusion of bacterially contaminated platelets.

Psoralens are naturally occurring compounds which have been used therapeutically for millenia in Asia and Africa. The action of psoralens and light has been used to treat vitiligo and psoriasis (PUVA therapy; Psoralen Ultra Violet A) and more recently various forms of lymphoma.

Psoralen will bind to nucleic acid double helices by intercalation between base pairs; adenine, guanine, cytosine and thymine (DNA) or uracil (RNA). Upon absorption of UVA photons the psoralen excited state has been shown to react with a thymine or uracil double bond and covalently attach to both strands of a nucleic acid helix.

Lethal damage to a cell or virus occurs when a psoralen intercalated into a nucleic acid duplex in sites containing two thymines (or uracils) on opposing strands sequentially absorb 2 UVA photons. This is an inefficient process because two low probability events are required, the localization of the psoralen into sites with two thymines (or uracils) present and its sequential absorption of 2 UVA photons.

U.S. Pat. No. 4,748,120 of Wiesehan is an example of the use of certain substituted psoralens by a photochemical decontamination process for the treatment of blood or blood products. The psoralens described for use in the process do not include halogenated psoralens, or psoralens with non-hydrogen binding ionic substituents. Using traditional psoralens such as 8-MOP, AMT and HMT, it is imperative that additives be added into the blood product solution in conjunction with U.V. irradiation in order to scavenge singlet oxygen and other highly reactive oxygen species formed by irradiation of the psoralen. Without the addition of reactive oxygen species scavengers, cellular components and protein components in the blood product are seriously damaged upon irradiation. (See also, U.S. Pat. No. 5,176,921.) It is clear, therefore, that irradiation of psoralens such as 8-MOP and AMT in aqueous solution creates a competition between the inefficient photocrosslinking reaction and the generation of highly reactive oxygen species. It is also possible that much of the viral deactivation seen using these photosensitizers actually results from the action of the reactive oxygen species against the viral contaminants rather than the inefficient photocrosslinking mechanism.

Attempts to inactivate viral decontaminants using photosensitizers and light have also been developed using some non-psoralen photosensitizers. The photosensitizers that have been employed are typically dyes. Examples include dihematoporphyrin ether (DHE), Merocyanine 540 (MC540) and methylene blue.

In any event, an effective radiation photosensitizer must bind specifically to nucleic acids and must not accumulate in significant amounts in lipid bilayers, which are common to viruses, erythrocytes, and platelets. Although there is evidence that psoralens bind to nucleic acids by intercalation, neutral psoralens such as 8-MOP (8-methoxypsoralen) are uncharged and thus also have a high affinity for the interior of lipid bilayers and cell membranes.

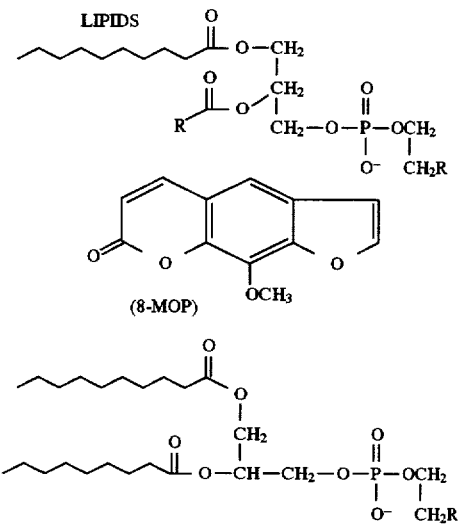

The binding of 8-MOP to cell membranes, shown above, would be acceptable if the psoralen bound to the lipid was photochemically inert. However, Midden (W. R. Midden, Psoralen DNA photobiology, Vol II (ed. F. P. Gaspalloco) CRC press, pp. 1, (1988) has presented evidence that psoralens photoreact with unsaturated lipids and photoreact with molecular oxygen to produce active oxygen species such as superoxide and singlet oxygen that cause lethal damage to membranes. Thus, it is believed that 8-MOP is an unacceptable photosensitizer because it sensitizes indiscriminate damage to both cells and viruses.

Positively charged psoralens such as AMT (4'-aminomethyl-4,5',8-trimethylpsoralen) will not bind to the interior of phospholipid bilayers (membranes) because of the presence of the charge. However, AMT contains an acidic hydrogen which can bind to the phospholipid head group by hydrogen bonding, shown below.

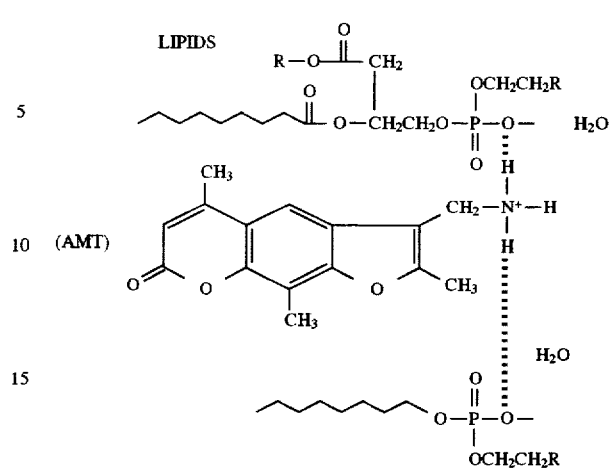

Thus AMT is believed to be an unacceptable photosensitizer because it will indiscriminately sensitize damage to viral membranes and to the membranes of erythrocytes and platelets.

Studies of the affects of cationic sidechains on furocoumarins as photosensitizers are reviewed in Psoralen DNA Photobiology, Vol. I, ed. F. Gaspano, CRC Press, Inc., Boca Raton, Fla., Chapter 2. The following points can be gleaned from this review:

1) The intent of this line of research was to improve the poor water solubility of the basic psoralen nucleus.
2) None of the psoralens described were halogenated as are the photosensitizers of the present invention.
4) Later conducted studies showed that a cationic group on a large linker, when added to the 5 or 8 position on the psoralen ring, gave the psoralen nucleus improved binding with native DNA relative to corresponding 5-MOP and 8-MOP analogues.
5) Sidechain substitution at the 5 position was found to be less desirable then substitution at the 8 position.
6) A study of 5-aminomethyl derivatives of 8-MOP showed that most of the amino compounds had a much lower ability to both photobind and form crosslinks to DNA compared to 8-MOP. These reports actually suggest that the primary amino functionality is the preferred ionic species for both photobinding and crosslinking.

U.S. Pat. No. 5,216,176 of Heindel describes a large number of psoralens and coumarins that have some effectiveness as photoactivated inhibitors of epidermal growth factor. Included among the vast functionalities that could be included in the psoralen or coumarin backbone were halogens and amines. The inventors did not recognize the significance of either functionality or the benefits of a photosensitizer including both functionalities.

U.S. patent applications Ser. Nos. 08/165,305 and 08/091,674 are commonly assigned with the present application, and are parent applications to this application. These applications disclose the use of a novel class of psoralen photosensitizers that are superior for use with irradiation to inactivate viral and bacterial contaminants in blood and blood products. The psoralens are characterized by the presence of a halogen substituent and a non-hydrogen binding ionic substituent to the basic psoralen side chain. See also, Goodrich et al. Proc. Natl. Acad. Sci. USA, 91:5552-56 (1994).

SUMMARY OF THE INVENTION

The present invention provides a method for the inactivation of viral and bacterial contaminants present in blood and blood protein fractions.

The present invention involves utilization of photosensitizers which bind selectively to a viral nucleic acid, coat protein or membrane envelope. The photosensitizer is also a moiety which can be activated upon exposure to radiation, which may be in the form of ultra-violet radiation or ionizing radiation, such as X-rays, which can penetrate the sample containing the contamination.

The present invention is also applicable to inactivation of blood-borne bacterial contaminants, and to blood-borne parasitic contaminants, since such infectious organisms rely on nucleic acids for their growth and propagation. Since purified blood plasma protein fractions are substantially free of human nucleic acids, and mature human peripheral blood cells, particularly red blood cells and platelets lack their own genomic DNA/RNA, the use of nucleic acid-binding photosensitizers is especially useful for the problem of treating blood contaminants.

The present invention may also be applied to viral inactivation of tissues and organs used for transplantation, and used in topical creams or ointments for treatment of skin disorders or for topical decontamination. The present invention may also be used in the manufacture of viral vaccines for human or veterinary use, particularly to produce live, nonviable or attenuated viral vaccines. The present invention may also be used in the treatment of certain proliferative cancers, especially solid localized tumors accessible via a fiber optic light device or superficial skin cancers.

The present invention utilizes a class of compounds that have a selective affinity to nucleic acid. The class of compounds also contains a halogen substituent and a water solubilization moiety, such as, quaternary ammonium ion or phosphonium ion. These materials comprise a relatively low toxicity class of compounds, which can selectively bind to the nucleic acid (single-stranded DNA, double-stranded DNA, or RNA) that comprise the genetic material of viruses. The bound compound can be activated by exposure to radiation, such as ultraviolet radiation (U.V. light of a defined wavelength), or ionizing radiation such as x-rays, after which the activated compound damages the bound viral nucleic acid or viral membranes rendering the virus sterile and non-infectious. Activation of the selectively bound chemical photosensitizer focuses the photochemistry and radiation chemistry to the viral nucleic acid or viral membranes and limits exposure to nearby cellular components or plasma proteins.

The preferred class of photosensitizers for use with the present invention are characterized generally as follows: a) they are intercalators, and they are comprised of either b) at least one halogen substituent or c) at least one non-hydrogen bonding ionic substituent. In preferred embodiments the photosensitizers comprise at least one halogen substituent and at least one non-hydrogen bonding ionic substituent. Particularly preferred photosensitizers are psoralens and coumarins comprising at least one halogen substituent and at least one non-hydrogen bonding ionic substituent.

In one embodiment of the present invention, the preferred photosensitizers are intercalators that fluoresce and that are comprised of either a) at least one halogen substituent or b) at least one non-hydrogen bonding ionic substituent. The preferred photosensitizers according to this embodiment are the substituted coumarins having the structure as shown below.

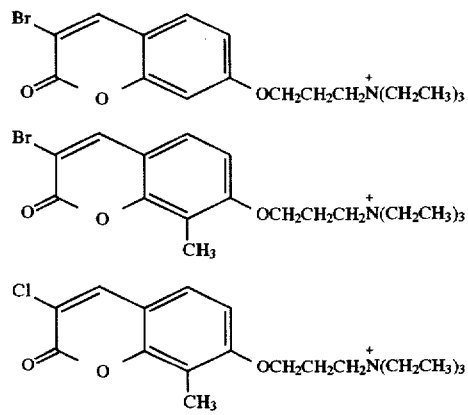

The photosensitizers disclosed herein are suited for the inactivation of a variety of viral and bacterial contaminants associated with blood and blood products. The present invention specifically includes the photo inactivation of blood and blood products contaminated with Human Immunodeficiency Virus-1 (HIV-1), Sindbis virus, Cytomegalovirus, Vesicular Stomatitis Virus (VSV), and Herpes Simplex Virus Type 1 (HSV-1), using the photosensitizers of the present invention.

The present invention also demonstrates the flexibility of adding one or more halogen atoms to any cyclic ring structure capable of intercalation between the stacked nucleotide bases in a nucleic acid (either DNA or RNA) to confer new photoactive properties to the intercalator. In the present invention essentially any intercalating molecule (psoralens, coumarins, or other polycyclic ring structures) can be selectively modified by halogenation or addition of non-hydrogen bonding ionic substituents to impart advantages in its reaction photochemistry and its competitive binding affinity for nucleic acids over cell membranes or charged proteins.

In one embodiment, halogenation of psoralen enables the molecule, once intercalated within the nucleic acid, to undergo a strand cleavage reaction upon light activation that non-halogenated psoralens cannot initiate. The nucleic acid strand cleavage is due to a novel electron transfer pathway (see FIG. 1) created by the breaking of the carbon-halogen bond upon input of appropriate radiation energy. The mechanism for this alternate chemical reaction requires a single photon of light and is more efficient than the crosslinking reaction that normally occurs with non-halogenated psoralens. In addition, as shown in FIGS. 1 and 2, the electron transfer reaction involves transfer from a donor (usually a guanine base when the intercalator is inserted in nucleic acid) and an acceptor (the carbon radical created by breakage of the carbon-halogen atom). Since the donor and acceptor species must be in close physical proximity for the transfer reaction to proceed, most damage is limited to the nucleic acid as desired for viral inactivation.

In a second embodiment, halogenation of a coumarin imparts totally new photoactive properties useful for viral inactivation. Coumarins, unlike psoralens, do not have an inherent ability to crosslink nucleic acid strands upon exposure to radiation, and hence have not heretofore found application as photosensitizers. However, as shown in the present invention (FIG. 2), halogenation of this class of intercalating molecules confers the ability to undergo the electron transfer mechanism, thereby imparting new properties to the molecule. Without intending to limit the present invention, the inventors believe that the example of coumarin halogenation demonstrates that these principles can be extended to any intercalating molecule, to confer new photoactive properties.

Due to the flexibility in adding halogen substituents or non-hydrogen bonding ionic substituents to virtually any cyclic or polycyclic ring structure, the inventors envision that new and useful molecules can be created by adapting the present invention to many known classes of ring compounds, whether those compounds comprise intercalating agents or not. For example, known classes of compounds that may be improved by the present invention include, porphyrins, phthalocyanines, quinones, hypericin, and many organic dye molecules (such as coumarins) including merocyanine dyes, methylene blue, eosin dyes, and others.

Without intending to limit the present invention, the inventors anticipate that new classes of compounds prepared according to the principles of this invention will find application in numerous fields in addition to decontamination of blood and blood products. The new chemical reaction properties imparted by halogenation and the selective binding properties imparted by the use of non-hydrogen bonding ionic substituents, may be grafted onto known classes of molecules to impart advantageous chemical reaction and targeting properties to these molecules. Psoralens for example, such as 8-methyoxypsoralen (8-MOP) have been used in therapeutic photopheresis to treat cutaneous T-cell lymphoma, scleroderma, and other cancers or skin disorders. The modified psoralen derivatives of the present invention (or other classes of compounds modified according to the present invention) may prove more efficacious in therapeutic photopheresis applications.

As a second example, organic dyes such as methylene blue (which is not considered a nucleic acid intercalating compound) have been used for viral inactivation treatments of blood plasma, with questionable success. It is contemplated that such organic dyes, modified according to the present invention, may prove more efficacious in such an application than the unmodified dye.

Without intending to limit the present invention, the inventors further anticipate that the fluorescent coumarin photosensitizers described herein may also be used in combination with known photosensitizing molecules that absorb in the visible light wavelength region. FIG. 11 shows the fluorescence emission spectrum of one such coumarin molecule. Photosensitizer A, having an emission peak at 414 nm in the visible light spectrum. The emission spectrum of Photosensitizer A extends beyond 500 nm, which can overlap the absorbance range of certain visible light activated molecules. It is therefore anticipated that a combination of a visible fluorescing photosensitizer with one or more photosensitizers that absorb in the visible light region may be utilized for enhanced virucidal or cytotoxic effect. Examples of photosensitizers that absorb in the visible light region include hypericin, pthalocyanines, porphyrins, and organic dyes such as methylene blue (see International Patent Application WO/94 14956 wherein hypericin is activated via a chemiluminescent reaction between luciferin and luciferase).

Other fields of application wherein the present invention may find application include the preparation of non-infectious viral vaccines, therapeutic treatment of immune system disorders by photopheresis, elimination of viable nucleated cells such as leukocytes via the cytotoxicity of nucleic acid binding photosensitizers, and possible treatment for certain accessible cancers and tumors, again exploiting the cytotoxic effects of nucleic acid binding photosensitizers.

The inventors further anticipate that the problem of singlet oxygen production by U.V. irradiation of traditional psoralen molecules can also be reduced by incorporating a quenching sidechain moiety onto the psoralen nucleus. An example of such a compound is shown below.

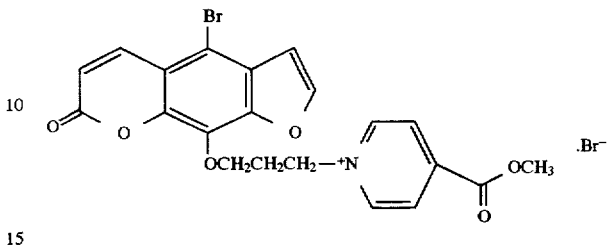

In this compound the non-hydrogen bonding ionic substituent of the present invention further comprises a quaternary ammonium pyridyl group. This quaternary ammonium pyridyl group will act as a quencher of the U.V. excited triplet state of the psoralen molecule (see FIG. 1).

While not intending to be bound by theory, in principle the quenching pyridyl group or a comparable functional group will deactivate the triplet state of any psoralen or intercalator, thereby preventing formation of undesired singlet oxygen. The pyridyl group quenches the excited triplet state by promoting electron transfer. In the presence of the pyridium ion the halointercalator serves as the donor, and carbon centered radicals are not formed. The electron is transferred from the halointercalator to the pyridium ion and back. This reversible electron transfer shorts out the triplet state before it can react to make singlet oxygen. (Although in principle the pyridium ions could quench the excited singlet state of the halointercalator, the lifetime of the singlet state is so short that little quenching would occur.)

Reduction of singlet oxygen production should minimize damage to lipid membranes or proteins. Attachment of a quenching group directly onto the psoralen nucleus provides proximity to the excited psoralen, and should obviate the need for addition of exogenous quenching agents (such as oxygen scavengers, reducing agents, or sugars) into the medium. Without limiting the scope of the present invention, the inventors anticipate that quenching sidechains that comprise both a non-hydrogen bonding ionic feature and a triplet quenching feature will be useful for selective viral inactivation of complex biological systems such as blood, blood plasma, or isolated blood cell fractions.

BRIEF DESCRIPTION OF THE DRAWINGS

FIG. 1 depicts the proposed energy diagram of photosensitizer A of the present invention.

FIG. 2 depicts the proposed reaction mechanism for the inactivation of nucleic acid upon irradiation of photosensitizer A.

DETAILED DESCRIPTION OF THE INVENTION

Figure 3:
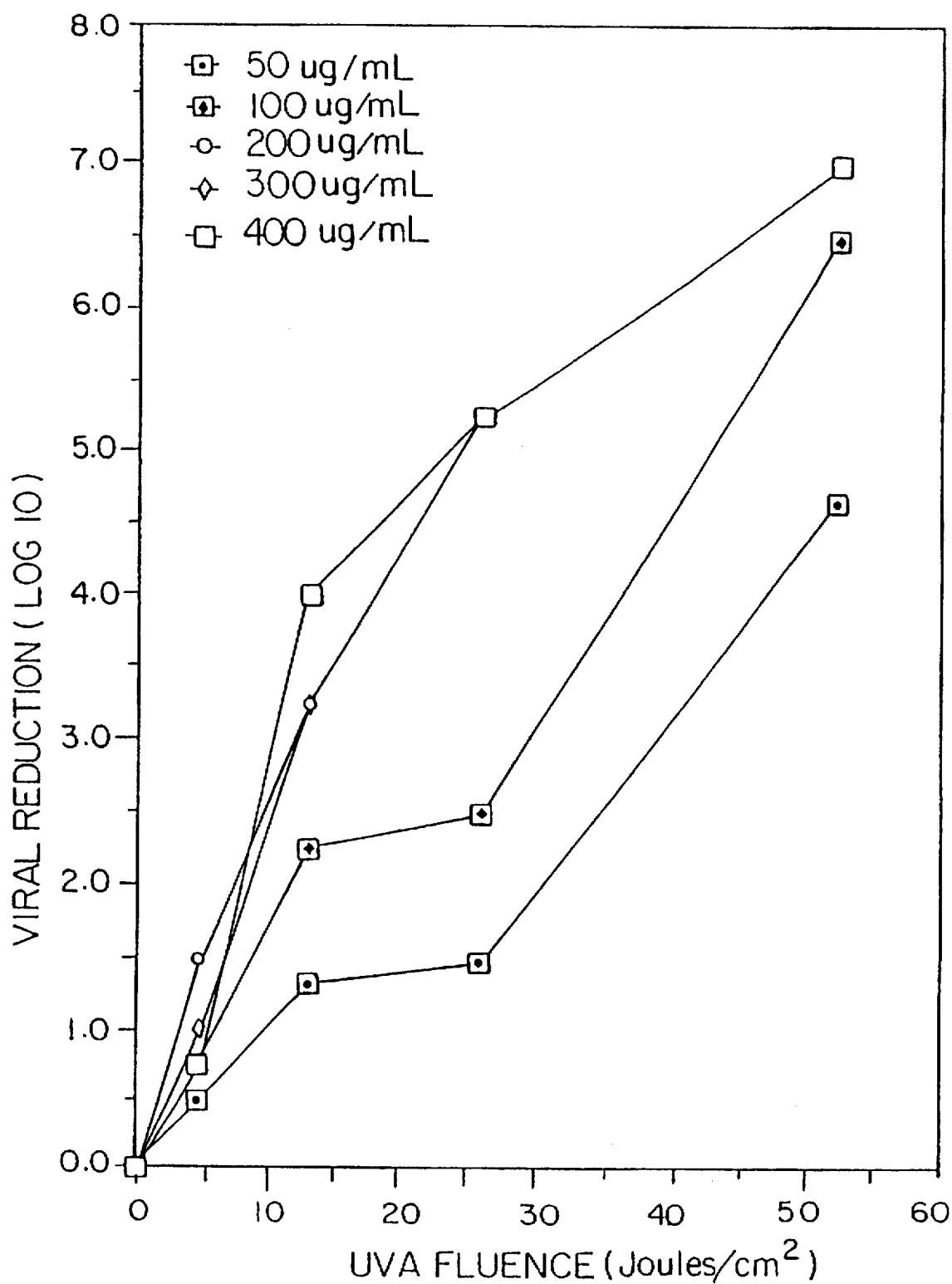
FIG. 3 depicts the inactivation of human immunodeficiency virus 1 (HIV-1) using long wavelength ultraviolet light (UVA) in the presence of different concentrations of photosensitizer B. Viral reduction (log 10) is plotted versus UVA fluence (Joules/cm$^2$).

The present invention is directed to methods for reducing viral, bacterial and other parasitic contamination in blood, blood components, cell cultures or cell culture components by irradiation in the presence of a chemical photosensitizer. Photosensitizers are disclosed which are particularly useful to decontaminate liquid compositions, such as blood, blood components, reconstituted lyophilized cells, and the like, using UV irradiation.

According to the present invention, a radiation sensitizing chemical compound is added to a liquid suspension of infectious viruses and/or bacteria and/or parasites, and the mixture is exposed to U.V. light or ionizing radiation. Assays of viral infectivity demonstrate the effectiveness of the compounds to inactivate the viruses, compared to radiation treatment alone.

The present invention includes a method for reducing viral, bacterial and other parasitic contamination from a biological solution. Biological solutions include, but are not limited to, solutions comprising blood, a blood component, cell culture or a component of a cell culture. The method comprises mixing the composition in a liquid state with a photochemical photosensitizer capable of binding to the viral, bacterial or parasitic contamination. The photochemical photosensitizer is capable of being activated by irradiation under conditions of sufficient wavelength, intensity and period of exposure to inactivate the contaminant, while at the same time the conditions for irradiation are insufficient to produce reactive oxygen species in the composition at levels which substantially impair the physiological activity of the treated composition. The composition containing the photosensitizer is then irradiated under conditions where the concentration of biologically active contaminant is reduced and the physiological activity of the composition is substantially unimpaired.

One of the most critical elements of the present invention is the use of a novel class of photosensitizer. A photosensitizer is defined for the purposes of this application as a chemical compound that has a light-absorbing chromophore that absorbs radiation in the ultraviolet or visible spectrum, and that is capable of inactivating viral or bacterial contaminants in blood or blood products.

The photosensitizers of the present invention are characterized by their ability to bind to the nucleic acid components of the viral or bacterial contaminants that are to be inactivated. The blood and blood product compositions that are to be treated according to the method of this invention all contain at least some cellular components or complex proteins.

In one embodiment of the invention, the photosensitizers of this invention are characterized as comprising a lipophilic moiety, a hydrophilic moiety and a photoreactive moiety.

The photosensitizers of this invention are preferably nucleic acid intercalators that are comprised of either 1) at least one halogen atom; and b) at least one non-hydrogen bonding ionic moiety. Intercalators are defined broadly herein as any chemical compound that has a specific affinity to double or single stranded nucleic acid. More specifically, intercalators are chemicals—not including nucleic acids, proteins or peptides—that locate themselves between neighboring base pairs in nucleic acids. Intercalators are generally characterized by the presence of a relatively planar rigid, multi-cyclic pi-conjugated chemical backbone. Those skilled in the art are familiar with a relatively large number of intercalators, and are generally able to predict the types of chemical species that are able to function as intercalators based on the chemical structure of the backbone of the chemical species. Psoralens and coumarins, which are the preferred basic structure for the intercalators of the present invention, are just two examples of chemical backbone structures capable of nucleic acid intercalation.

Preferred photosensitizers of the present invention comprise at least one halogen substituent. The halogens include F, Cl, Br and I. In the preferred embodiments of the present invention, the photosensitizer contains at least one bromine or chlorine atom.

Preferred photosensitizers of the present invention comprise at least one non-hydrogen bonding ionic substituent. Chemical functionalities that are ionic and non-hydrogen bonding include quaternary ammonium functionalities and phosphonium functionalities. A variety of additional functionalities that are both ionic and non-hydrogen bonding are familiar to those skilled in the art, and equally applicable for use with this invention.

In the preferred embodiments of the invention, the non-hydrogen bonding ionic substituent is linked to the backbone of the chemical intercalator via a spacer unit. The spacer can be selected from any of a number of chemical subunits known to those skilled in art, but in the preferred embodiments is composed of a saturated linear alkoxy group. In the most preferred embodiment the spacer element is —O(CH$_2$)$_3$—.

The most preferred non-hydrogen bonding ionic functionalities are quaternary ammonium functionalities, more specifically trialkyl quaternary ammonium and even more specifically —O(CH$_2$)$_3$ N$^⊕$(CH$_2$CH$_3$)$_3$.

Two preferred photosensitizers of the present invention are the following:

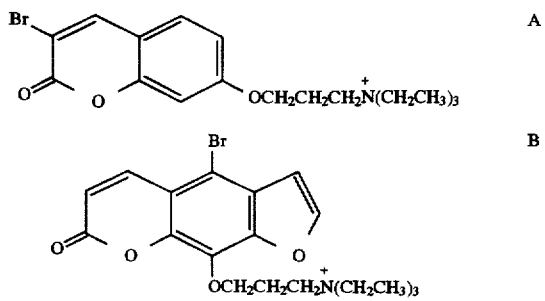

Compound A is a coumarin based photosensitizer, and compound B is a psoralen or furocoumarin based photosensitizer.

Additional preferred embodiments of the present invention include the following coumarin based photosensitizers:

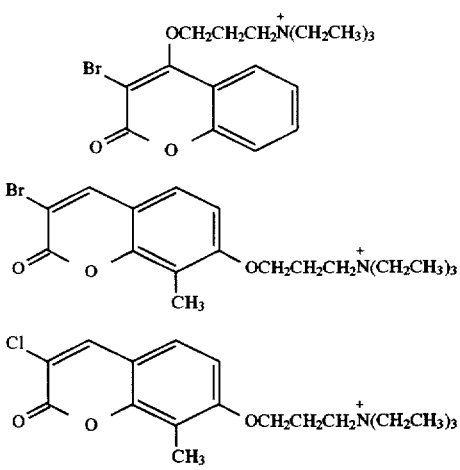

Figure 7:
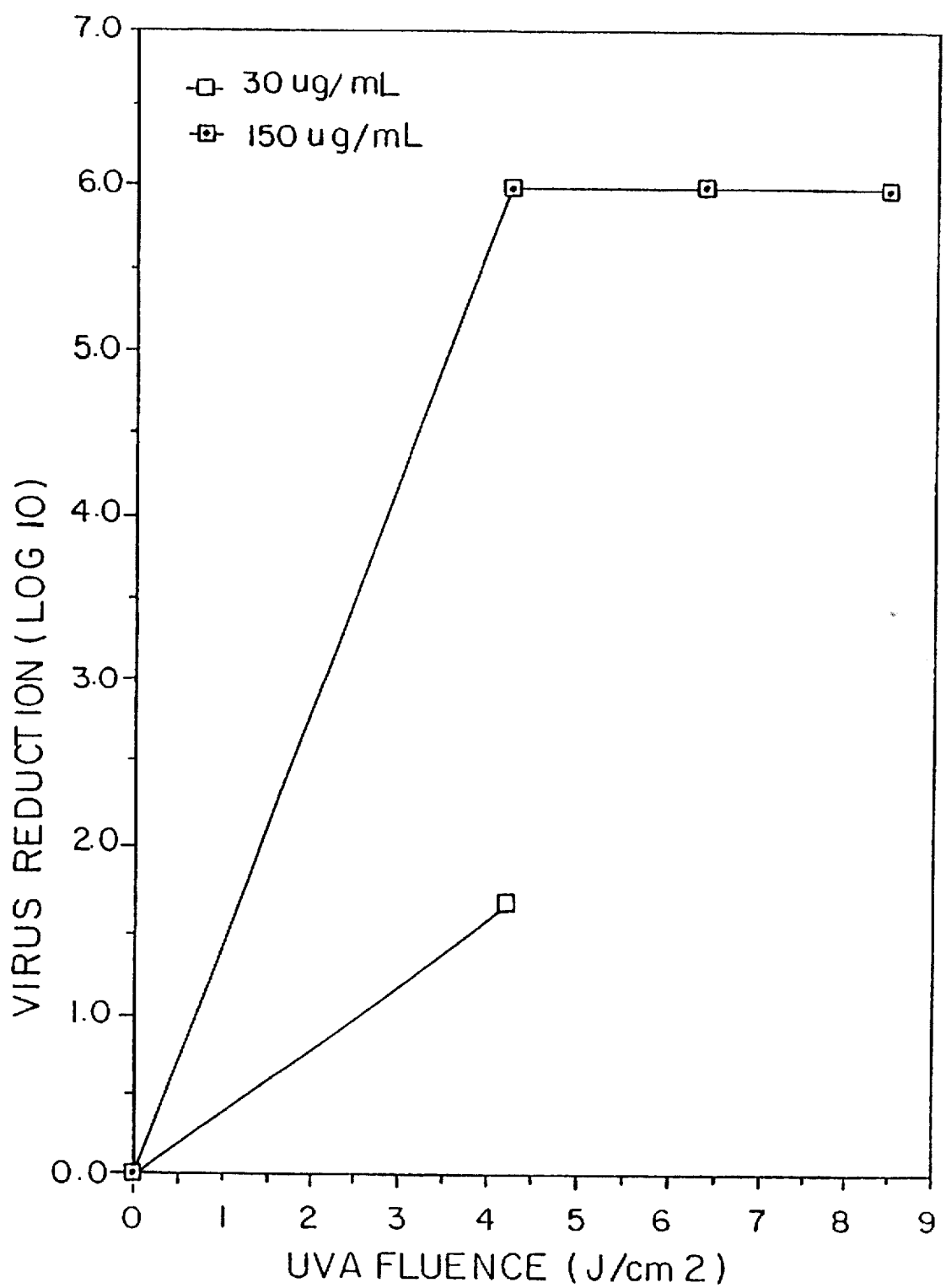
FIG. 7 depicts the inactivation of Vesicular Stomatitis Virus (VSV) in platelet concentrate using photosensitizer B and UVA. Viral inactivation is plotted versus UVA fluence.
Figure 13:
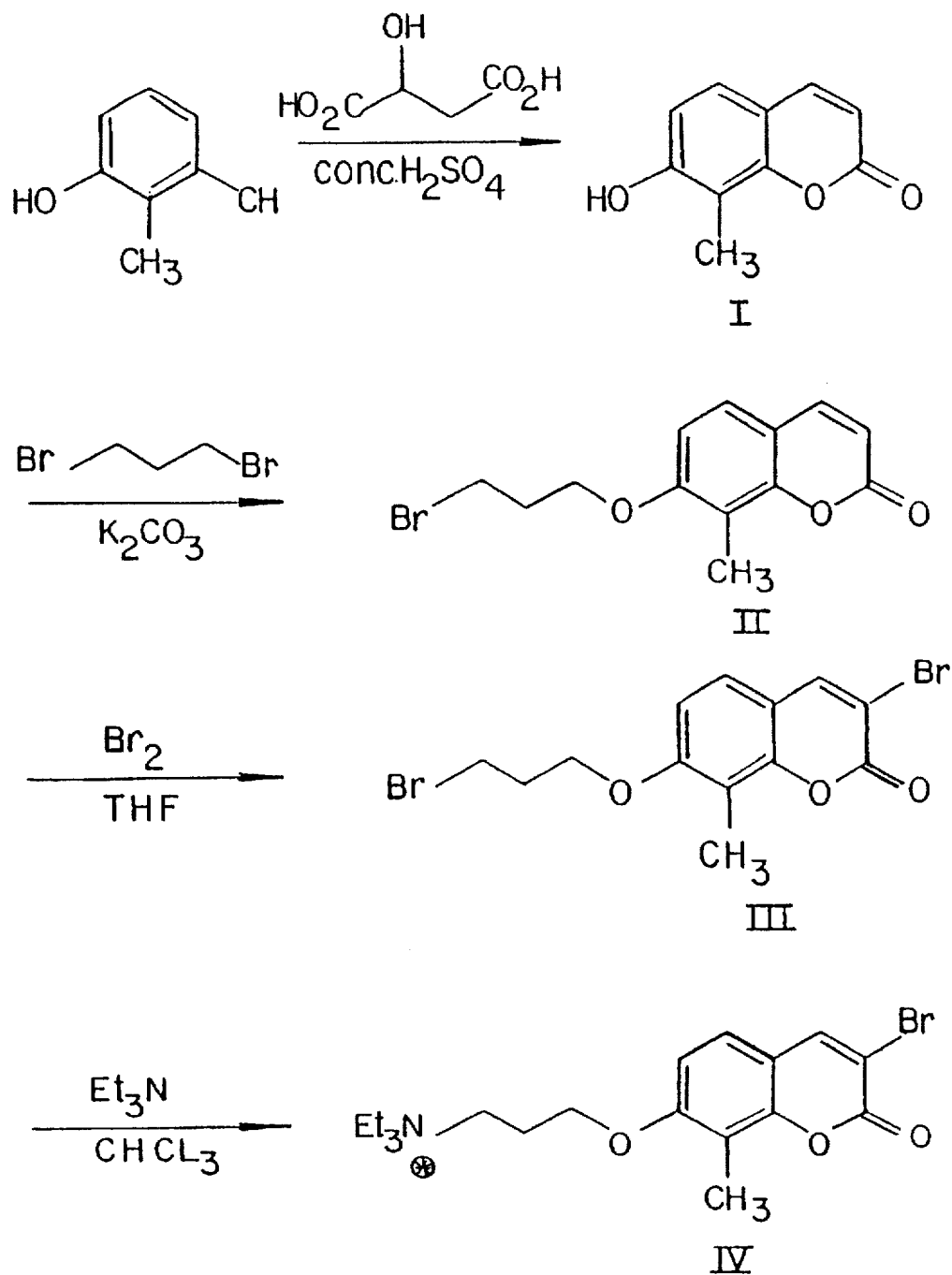
FIG. 13 depicts the synthetic scheme for the synthesis of photosensitizer D.

The synthesis of photosensitizer A is described in Example 9 below, according to the scheme shown in FIG. 7. The synthesis of photosensitizer D is described in Example 14 below, according to the scheme shown in FIG. 13.

Upon irradiation with U.V. light, compound A has been shown to be effective at viral inactivation while compound B has been shown to be effective at viral and bacterial inactivation. Compounds A, D and E also fluoresce upon U.V. irradiation. It is theorized by the present inventors that the fluorescence pathway for the dispersion of energy from the excited state of irradiated compounds A, D and E as depicted in FIG. 1, acts to reduce the production of highly reactive oxygen species in blood and blood components. The proposed reaction mechanism for the inactivation of viral contaminants using compound A and light is shown in FIG. 2. According to the proposed mechanism—which is speculative and not intended to limit the scope of the invention—the photoreaction is initiated by an electron transfer from a guanine residue to the photosensitizer in its executed singlet state. Electron transfer is followed by Br-C bond homolysis and the generation of a coumarin radical that can attack the nucleic acid backbone.

Bromopsoralens, and photosensitizer B specifically, do not form free radicals upon irradiation in solution. A donor is required to activate photosensitizer B. Using fluorescence spectroscopy it has been shown that amino acids are not suitable donors to activate photosensitizer B. Thus any of these photosensitizers bound or associated with proteins should not generate radicals capable of damaging proteins.

It is therefore one preferred embodiment of the method of the present invention to use a photosensitizer that is capable of fluorescence. Coumarins and furocoumarins that fluoresce are known to those skilled in the art, and the screening of photosensitizers to determine fluorescent properties is easily determined.

Photosensitizers that are capable of fluorescence appear to be superior to non-fluorescent varieties. For a photosensitizer to be useful, there must be a mechanism for viral and bacterial inactivation. Non-halogenated psoralens may still function as useful photosensitizers if they are properly situated in the solution to be treated. Such compounds can inactivate viruses via the traditional photocrosslinking mechanism. Other photosensitizers, such as those having the coumarin backbone structure, must be halogenated in order to accomplish significant viral or bacterial inactivation. Thus, in this embodiment of the invention the preferred photosensitizers are intercalators, are capable of fluorescence; and either 1) are halogenated; or 2) have the psoralen backbone structure.

According to an additional embodiment of the present invention, the photosensitizer of the invention may comprise a quenching sidechain moiety attached to the intercalating backbone. FIG. 1 provides a diagrammatic energy diagram for certain halogenated photosensitizers that are capable of fluorescence. According to the theory expressed herein, the ability to fluoresce provides a rapid means for the excited singlet state species to revert to ground energy state that competes with intersystem crossing to the triplet excited state. For photosensitizers that do not fluoresce in particular, the presence of a quenching moiety attached to the intercalator can also serve the same function.

An example of a photosensitizer of this embodiment of the invention is as follows:

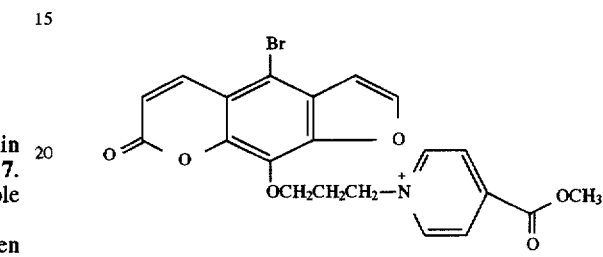

The non-hydrogen bonding ionic substituent comprises a quaternary ammonium pyridyl group. Such a compound can be easily prepared by one skilled in the art without undue experimentation. The quaternary ammonium pyridyl group can serve as a quencher of the U.V. excited triplet state of the Psoralen compound. While not intending to be bound by theory, it is proposed that the quenching group will deactivate the triplet state of any intercalator, thereby preventing formation of undesired singlet oxygen. The reduction of singlet oxygen production as such minimizes damage to lipid membranes or proteins. The proximity of the quenching moiety to the intercalator should make quenching highly preferred to any reaction with oxygen in solution, and should also obviate the need for the addition of exogenous quenching agents (such as oxygen scavengers, reducing agents or sugars) into the medium. The quenching moiety may be attached to the backbone of the photosensitizer at any position, and can consist of any chemical functionality known to those skilled in the art to function as an excited state quenching agent.

The quaternary ammonium or phosphonium substituted halo-intercalators described herein do not accumulate in the interior of lipid bilayers (membranes) found in blood and blood products because of the presence of the charge, nor will they bind to the phospholipid head groups of the membrane because they lack acidic hydrogen for hydrogen bonding.

Prior art psoralens (such as 8-MOP and AMT) must often be used in combination with a quencher (e.g. mannitol, dithiothreitol, vitamin E, etc.) to protect, repair or otherwise offset the deleterious effects of the photosensitizer and light on cell membranes, and to quench the production of free oxygen radicals in solution that cause indiscriminate damage. The photosensitizers described herein do not accumulate in viral membranes and as a consequence do not require the presence of a quencher additive to the blood product. In addition, the photosensitizers described herein containing halogen also should generate a minimal amount of free radicals in solution, thereby avoiding the need for quenchers.

One preferred class of photosensitizers is selected from the group consisting of compounds of the formula (I):

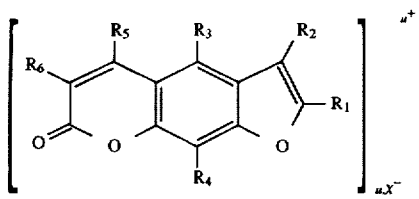

wherein u is an integer from 1 to 6; X is an anionic counterion; Z is N or P; $R_1$, $R_2$, $R_3$, $R_4$, $R_5$, and $R_6$ are independently halo; H; linear or branched alkyl of 1–10 carbon atoms; linear or branched alkoxy of 1–10 carbon atoms; $(CH_2)_m$—$O(CH_2)_p Z_{61}R'R''R'''$ or —$O(CH_2)_n Z_{61}R'R''R'''$ wherein n, m and p are independently integers from 1 to 10 and R', R", and R'" are independently H or linear or branched alkyl of 1 to 10 carbon atoms with the proviso that on each Z atom, not more than two of R', R", or R'" may be H; and at least on one of $R_1$, $R_2$, $R_3$, $R_4$, $R_5$ or $R_6$ is $(CH_2)_m O(CH_2)_p Z_{61}R'R''R'''$ or —$O(CH_2)_n Z_{61}R'R''R'''$. Particularly preferred are compounds wherein $R_4$ is —$O(CH_2)_n N \oplus R'R''R'''$, $(CH_2)_m$—$O(CH_2)_p Z_{61}R'R''R'''$, especially wherein R', R" and R'" are ethyl and n=3. Preferably, $R_6$, $R_5$, $R_2$ and $R_1$ are hydrogen and $R_3$ is H or halo, preferably bromo.

wherein u is an integer from 1 to 6; X is an anionic counterion; Z is N or P; $R_1$, $R_2$, $R_3$, $R_4$, $R_5$, and $R_6$ are independently halo; H; linear or branched alkyl of 1–10 carbon atoms; linear or branched alkoxy of 1–10 carbon atoms; $(CH_2)$—$_m O(CH_2)_p Z \oplus R'$, R", R'" or —$O(CH_2)_n Z_{61}R'R''R'''$ wherein n, m and p are independently integers from 1 to 10 and R', R", and R'" are independently H or linear or branched alkyl of 1 to 10 carbon atoms with the proviso that on each Z atom, not more than two of R', R", or R'" may be H; and at least on one of $R_1$, $R_2$, $R_3$, $R_4$, $R_5$ or $R_6$ is $(CH_2)_m O(CH_2)_p Z_{61}R'R''R'''$ or —$O(CH_2)_n Z_{61}R'R''R'''$. Particularly preferred are compounds wherein $R_4$ is —$O(CH_2)_n Z \oplus R'R''R'''$, especially wherein R', R" and R'" are ethyl and n=3. Preferably, $R_3$, $R_5$, $R_2$ and $R_1$ are hydrogen and $R_3$ is H or halo, preferably bromo.

In general, the above compounds may be made by halogenating psoralens and isolating the appropriately substituted isomers. For compounds wherein the ring substituent is a quaternary ammonium alkoxy or phosphonium alkoxy group, that group may be made from the corresponding hydroxy-substituted psoralens, as exemplified by the following scheme.

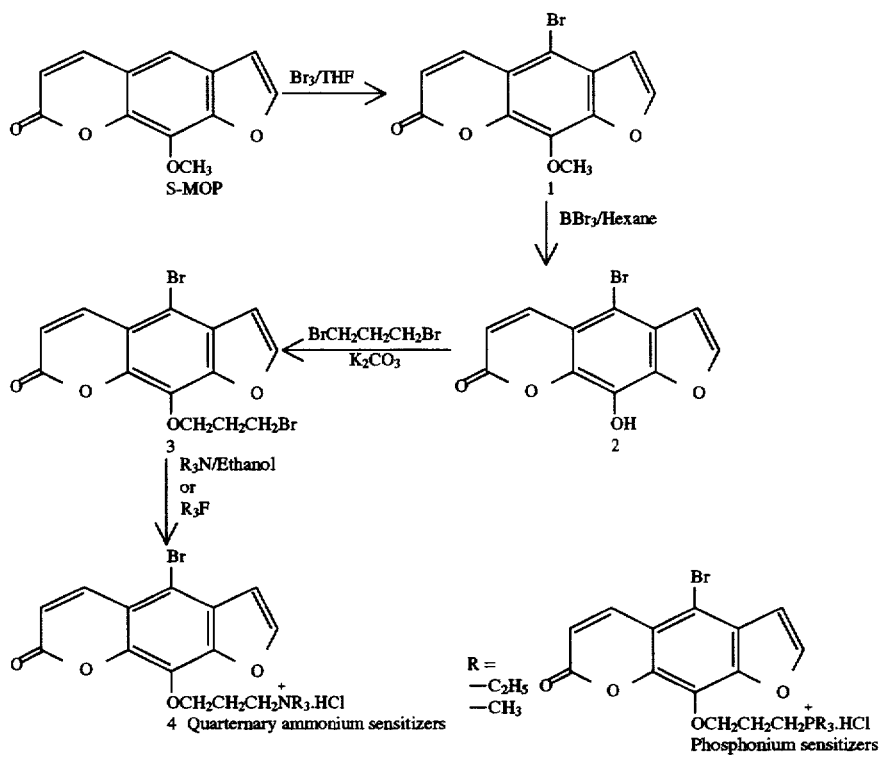

An additional preferred class of photosensitizers is selected from the group consisting of the formula (II).

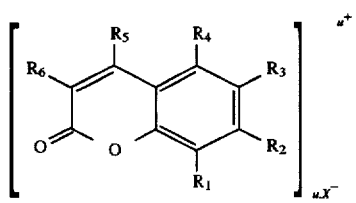

As described above, the most preferred photosensitizers of the present invention are comprised of ionic functionalities that are non-hydrogen bonding. However, included within the scope of this invention are photosensitizers comprised of amine functionalities having one and in some cases two amine hydrogens. These compounds, of course, are capable of forming hydrogen bonds. It has been shown that there is a direct correlation between the number of hydrogens available on the amine and the cellular destruction-caused by a class of psoralen compounds. Goodrich, et al. Proc. Nat'l. Acad. Sci. USA. 91:5552–56 (1994). Thus, photosensitizers containing amine functionalities having two hydrogens are less preferred than those having one hydrogen, which are in turn less preferred than those having no hydrogen attached to the amine.

Therefore, according to this invention, sensitizing compounds for viral inactivation preferably do not contain substituents which possess free hydrogen groups capable of exhibiting hydrogen bonding to the cell membrane.

From the foregoing description, it will be realized that the invention can be used to selectively bind a chemical photosensitizer to blood-transmitted viruses, bacteria, or parasites. Also monoclonal or polyclonal antibodies directed against specific viral antigens (either coat proteins or envelope proteins) may be covalently coupled with a photosensitizer compound.

Since cell compositions also comprise a variety of proteins, the method of decontamination of cells described herein is also applicable to protein fractions, particularly blood plasma protein fractions, including, but not limited to, fractions containing clotting factors (such as Factor VIII and Factor IX), serum albumin and/or immune globulins. The viral and bacterial inactivation may be accomplished by treating a protein fraction with a photosensitizer as described herein.

Although described in connection with viruses, it will be understood that the methods of the present invention are generally also useful to inactivate any biological contaminant found in stored blood or blood products, including bacteria and blood-transmitted parasites.

The halogenated psoralens and coumarins according to the present invention are improved and more efficient photosensitizers because they require only a single UVA photon for activation. The ability of the halogen photosensitizer to react with any base pair imposes no limitation for the site of intercalation. As shown in FIG. 2, absorption of a UVA photon by a bromocoumarin in the presence of guanine (or any nucleotide base) leads to electron transfer and the formation of bound radicals and ultimately nucleic acid cleavage and viral or cell death. This cleavage mechanism is more efficient than the conventional crosslinking reaction of non-halogenated psoralens.

The coumarin radical 2 (FIG. 2) can inflict damage on the nucleic acid double helix to which it is bonded by abstraction of a ribose (RNA) or deoxyribose (DNA) sugar carbon hydrogen bond. This can lead to DNA cleavage by known mechanisms. The guanine radical cation shown as an example is also known to react with molecular oxygen, initiating a series of reactions which cleave DNA. The byproduct of the bound radical photochemistry is debrominated coumarin 4, which is incapable of forming crosslinks to DNA unlike psoralens.

A preferred class of photosensitizers comprise nucleic acid intercalators which may be added to plasma or plasma fractions followed by UV radiation to reduce the viral contamination therein. According to the present invention, the reduction of viral contamination can be unexpectedly reduced by utilizing halogenated intercalators. For example, it was observed that the bromopsoralens are about 200,000 times more effective in reducing viral activity when compared to use of their non-brominated counterparts.

The brominated intercalators are an improvement over the known psoralens and other substituted psoralens when used as photosensitizers because only one photon of light is required to activate the brominated photosensitizer whereas two photons are required to activate a non-brominated photosensitizer. Secondly, a brominated intercalator is effective in virtually every intercalative site, whereas a non-brominated photosensitizer is effective only in intercalation sites containing a uracil or thymine on different strands of the DNA or RNA. The brominated intercalators are also an improvement over the known coumarins, which unlike the known psoralens have no crosslinking ability and therefore have generally not been used previously as photosensitizers for viral inactivation, or as light activated drugs in therapeutic photopheresis procedures for certain cancer treatments and immune disorders.

The use of the brominated or halogenated intercalators is particularly useful for activation in hydrated systems such as plasma, immune sera, tissue culture media containing animal serum or serum components (such as fetal calf serum), or recombinant products isolated from tissue culture media.

The present invention may be applied to treatment of liquid blood in ex vivo irradiation, such as by methods and apparatus described in U.S. Pat. Nos. 4,889,129 and 4,878,891 and 4,613,322.

The photosensitizers also may be utilized in vivo and delivered in liposomes (artificial cells) or drug-loaded natural cells. After introduction of the liposome or drug-loaded cell, the patient may be treated by radiation to activate the photosensitizer.

The present invention is applicable to contaminants which comprise single or double-stranded nucleic acid chains, including RNA and DNA, and viruses, bacteria or other parasites comprising RNA and/or DNA.

Figure 4:
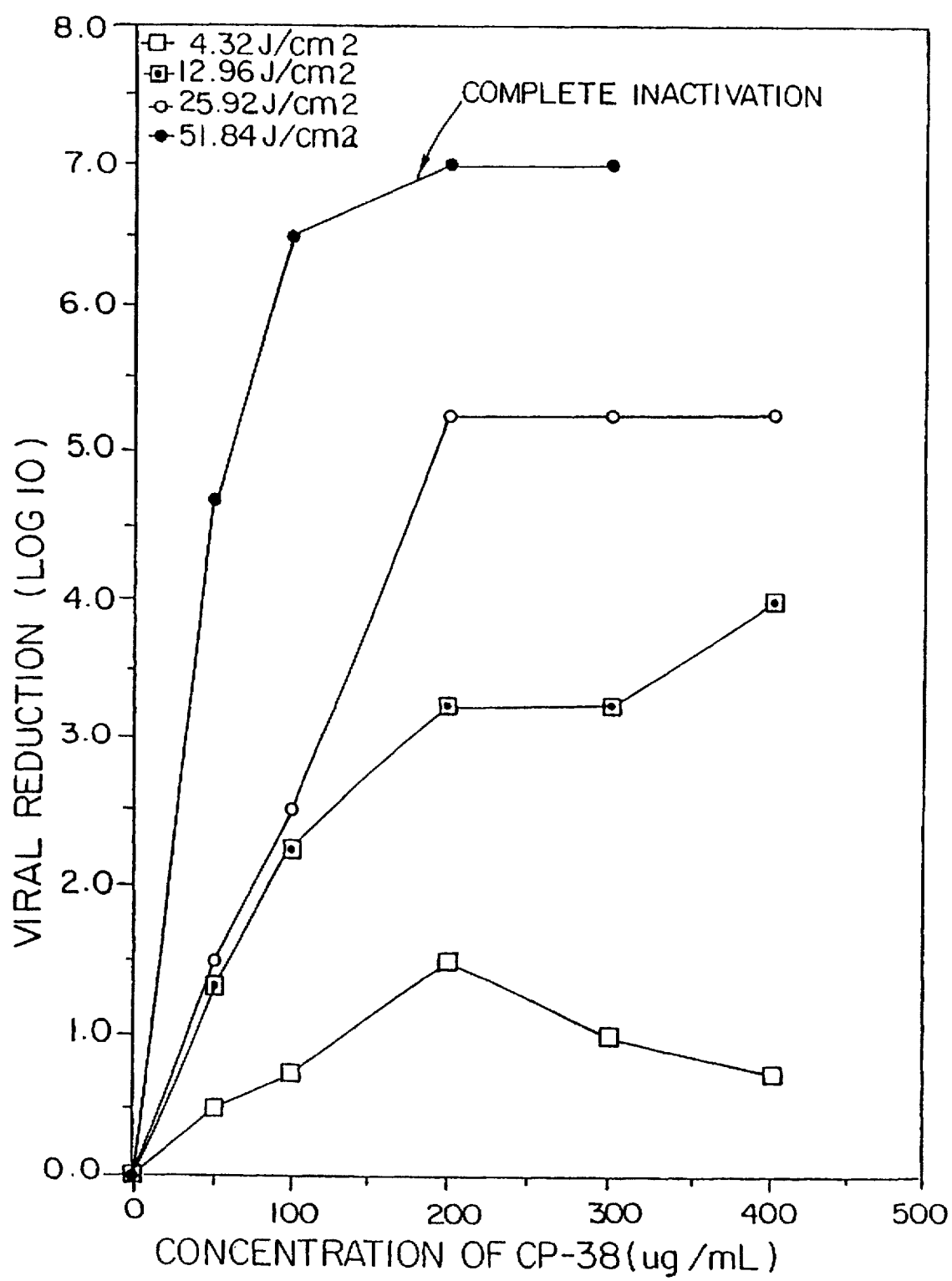
FIG. 4 depicts the same data as FIG. 3 above, where viral reduction is plotted versus concentration of photosensitizer B.

The present invention includes the inactivation of specific viral species that are found as contaminants in blood and blood products. Example 1 below describes in great detail the experimental protocol for the inactivation of HIV-1 virus in platelet concentrate. The results obtained from this series of experiments validates the ability of the photosensitizers of the present invention to inactivate HIV-1 virus in a blood product. The results of this study are summarized in Table 1. Reductions in viral titer were obtained by subtracting the viral titer of treated samples from control samples. FIG. 3 and 4 show the results of the study graphically. FIG. 3 shows the viral reduction versus light intensity for a number of different concentrations of photosensitizer B, and FIG. 4 shows viral reduction versus concentration of photosensitizer B.

Figure 5:
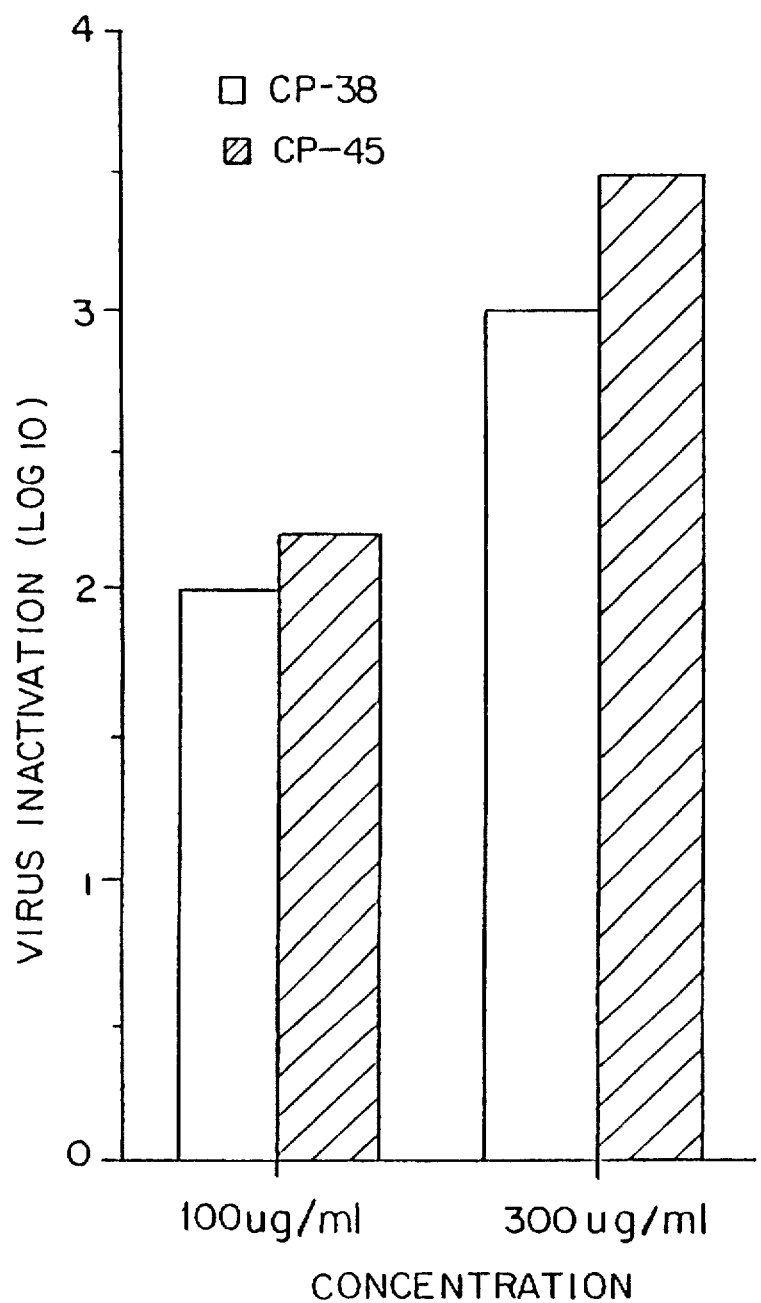
FIG. 5 depicts the inactivation of Sindbis virus with photosensitizer A and photosensitizer B. Virus inactivation is shown versus concentration of photosensitizer.
Figure 6:
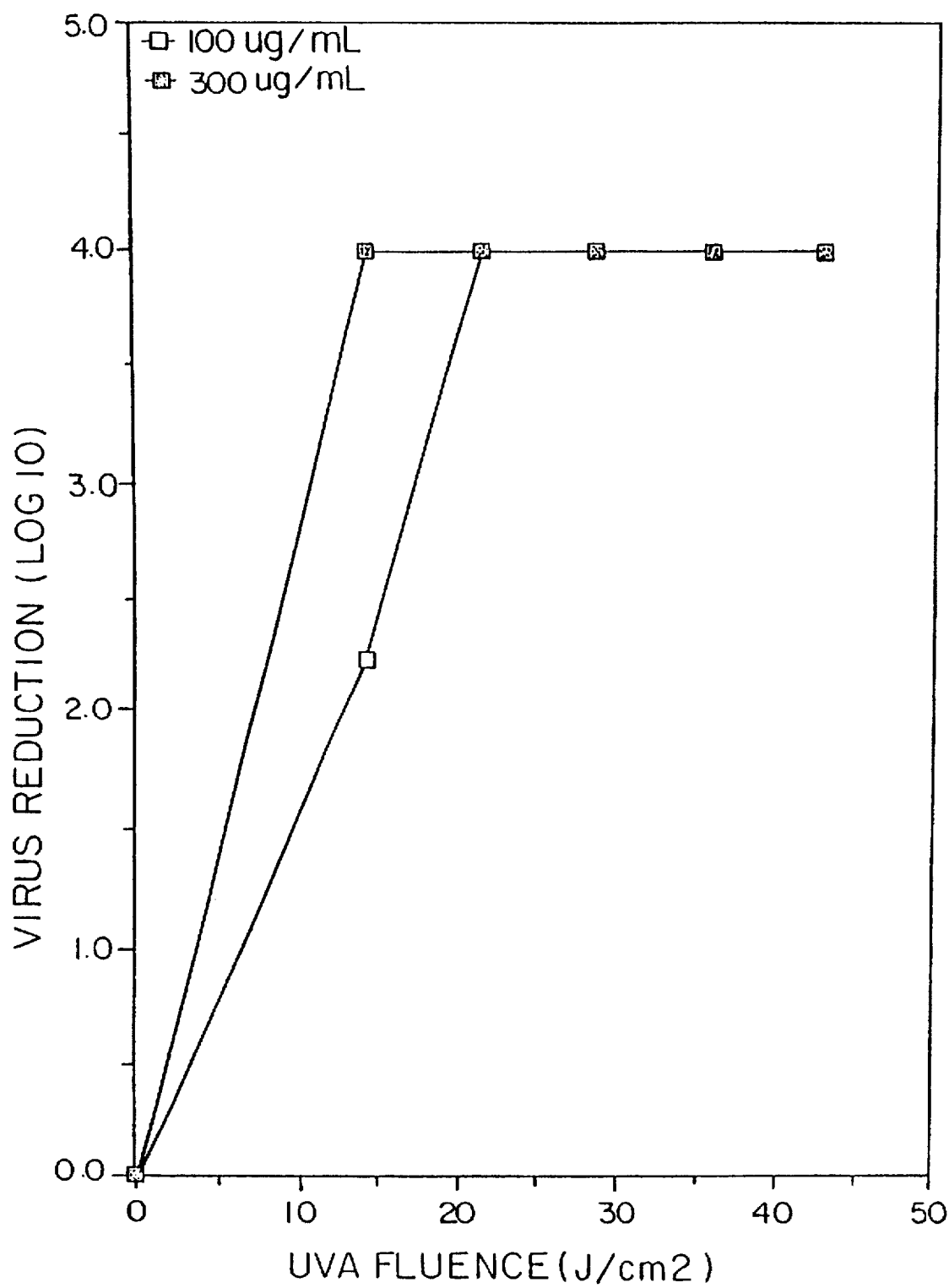
FIG. 6 depicts the inactivation of Cytomegalovirus using photosensitizer B and UVA. Viral inactivation is plotted versus UVA fluence.
Figure 8:
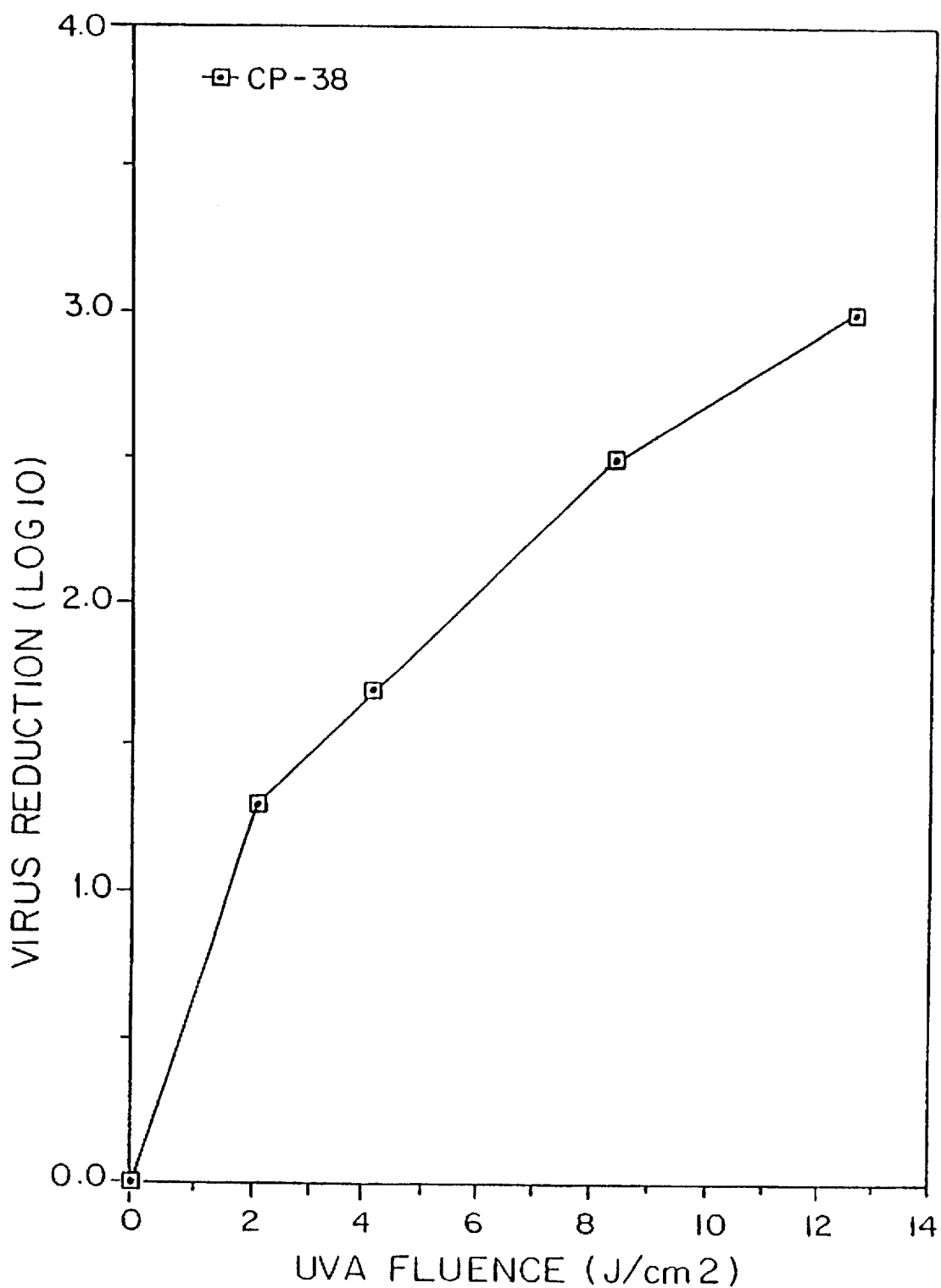
FIG. 8 depicts the inactivation of Herpes Simplex Virus Type 1 (HSV-1) in the presence of photosensitizer B and UVA. Viral inactivation is plotted versus UVA fluence.

The procedure described in detail in Example 1 for the inactivation of the HIV-1 virus in platelets was typical of the type of experimental protocol utilized to examine the inactivation of a variety of viral species. Example 2 below describes the general protocol used to demonstrate the inactivation of Sindbis virus in human plasma. The results of the inactivation using photosensitizer A and photosensitizer B are depicted in FIG. 5. Example 3 below describes the general protocol used to demonstrate the inactivation of Cytomegalovirus in human platelet concentrates. The results of the inactivation using photosensitizer B are depicted in FIG. 6. Example 4 below describes the general protocol used to demonstrate the inactivation of Vesicular Stomatitis Virus in human platelet concentrates. The results of the inactivation using photosensitizer B are depicted in FIG. 7. Example 5 below describes the general protocol used to demonstrate the inactivation of Herpes Simplex Virus Type I. The results of the inactivation using photosensitizer B are depicted in FIG. 8.

Because the photosensitizers of the present invention are to be used to inactivate blood and blood products that will be used for transfusion into human patients, it is imperative that they be safe for transfusion following irradiation. Example 6 below describes the mutagenicity protocol used to verify the safeness of the photosensitizers of the present invention. The specific example provided in this example is for photosensitizer B, before and after irradiation, under conditions suitable for the inactivation of viral and bacterial components in blood and blood products. The results of the mutagenicity tests for photosensitizer B demonstrate that a mixture of photosensitizer B photolysis products and a maximum residual photosensitizer B concentration of 4.36 µg/mL per test plate did not cause any mutagenic effects in Salmonella strains TA98, TA100, TA1535, TA1537 and TA1538. The maximum residual concentrations of photosensitizer B under use conditions (25J/cm$^2$ of UVA) corresponds to about 3.4 times the expected concentration of photosensitizer B per therapeutic dose of platelet concentrates of 1.28 µg/mL. The results thus demonstrate that photosensitizer B is non-mutagenic when photolyzed in platelet concentrates such that the initial concentration is reduced by at least 60% under used conditions (>25 J/cm$^2$ UVA and 12.8 µg/mL photosensitizer B plate).

The mutagenicity results for photosensitizer A showed that for both irradiated and non-irradiated solutions there was no significant increase in reversion rate with any of the five tester strains in the absence or presence of S-9 activation.

Example 7 describes the mouse fibroblast protocol used to determine the cytotoxicity of the photosensitizers of the present invention. The results of these tests for photosensitizer B at 72 hr are depicted in Table 2. Example 8 describes the Chinese Hamster Ovary, Hybridoma Cells and AE-L Cells protocol used to determine the cytoxicity of the photosensitizers of the present invention. The results of these tests for photosensitizer B are depicted in Tables 3 and 4.

Figure 9:
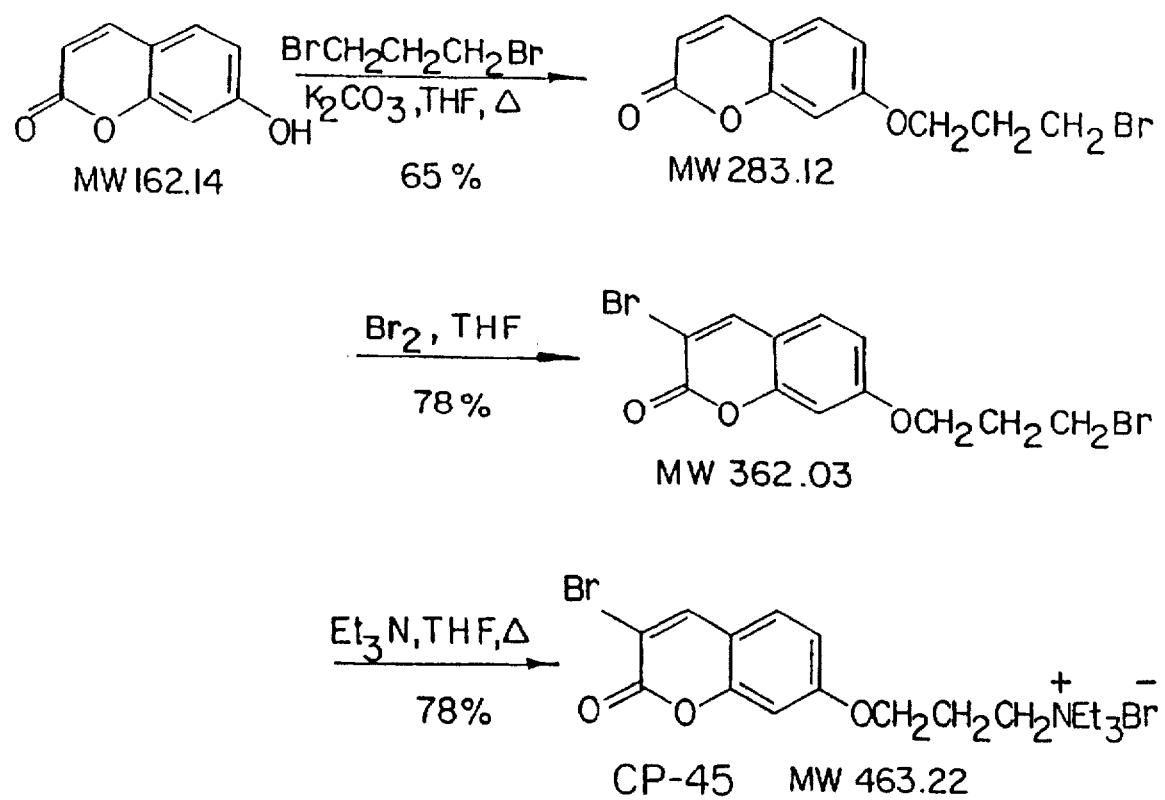
FIG. 9 depicts the synthetic scheme for the synthesis of photosensitizer A.

Compound A, 3-bromo-7-(γ-triethylammonium propyloxy) coumarin bromide, is one of the most preferred photosensitizers of the present invention. The synthesis of Compound A is given in Example 9. The reaction scheme for the synthesis is shown in FIG. 9.

One of the best measures of the effectiveness of potential photosensitizers is the extent to which the photosensitizer tends to associate with nucleic acids rather than to cellular membrane components or proteins in blood or blood products. Example 10 below describes the protocol that was employed for analyzing the specificity a variety of photosensitizers have for nucleic acids.

Independent of the mechanism of photosensitized inactivation of viral and bacterial contaminants in blood or blood products, it is generally clear that the greater the preference the photosensitizer has to the nucleic acid components of the contaminants—as opposed to cellular membranes or proteins in solution—the better the performance of the photosensitizer. The quality of a photosensitizer being determined by the rate efficiency of contaminant inactivation, absolute contaminant inactivation, and as little impairment of the physiological activity of the treated composition as possible. Of course these factors are interrelated. The results of specificity experiments comparing the photosensitizers of the present invention with prior art photosensitizers reveals the superior properties of the novel photosensitizers disclosed herein. These results are shown in Table 5.

The photosensitizers of the present invention have been examined to show the effects on the constituents of platelet concentrates under conditions that are sufficient for obtaining complete contaminant inactivation. The general procedure for conducting these experiments is disclosed in Example 11 below.

Table 6 presents a summary of the in vitro platelet properties after photoactivation in the presence of 300 µg/mL of photosensitizer B, with and without bicarbonate. The bicarbonate was added to offset the effects on the pH of the solution that result from irradiation. Table 7 presents a summary of the pheresed platelet in vitro properties following photoinactivation in the presence 300 µg/mL of photosensitizer B. Table 8 summarizes the platelet in vitro properties following photoinactivation in the presence of photosensitizer A. The pH does not substantially change when photosensitizer A is employed.

Additional experiments were conducted in order to compare the photosensitizers of the present invention with two prior art photosensitizers, 8-MOP and AMT. The protocol for this evaluation of photosensitizers irradiated in human platelet concentrates is described in Example 12 below. The results of this comparison can be summarized as follows:

1. Complete inactivation of bacteriophage φ6 ($\geq 6$ logs of viral reduction) was obtained with photosensitizer B without alteration in platelet in vitro properties (HSR, morphology, aggregation response to collagen) under normal oxygen content at UVA fluence of 7.6 J/cm$^2$.

2. Equimolar concentrations of AMT and 8-MOP required 45 and 68 J/cm$^2$ of UVA energy respectively to obtain greater than 4 logs of viral inactivation. These conditions were associated with major alterations in platelet in vitro properties.

3. Photoinactivated platelet concentrates using photosensitizer B (60 µm photosensitizer concentration and 4.5 J/cm$^2$) maintained normal properties following post-treatment storage for 5days in a standard platelet incubator at 22±2° C.

4. Virucidal efficacy of brominated psoralen was substantially higher than that for 8-MOP and AMT with respect to inactivation of non-enveloped bacteriophages such as lambda and R-17.

Example 13 describes the results of a comparison study of the ability of a variety of photosensitizers of the present invention to inactivate sindbis virus in human plasma. The compounds tested in this series of experiments were photosensitizers A, B, D and E, and non-halogenated forms of A, C and D. The results of these experiments are depicted graphically in FIG. 12. The results show that under the same conditions: 1) the coumarin-based photosensitizers A, C and D are superior to the psoralen-based photosensitizer B; 2) the non-halogenated coumarin-based photosensitizers are not suitable for photoactivated inactivation of virus; and 3) the methylated coumarins, photosensitizers D and E, appear to be the most efficient photosensitizers for viral inactivation.

Example 14 describes the synthesis of photosensitizer D. The procedure follows the synthetic scheme depicted in FIG. 13. Following this general procedure, which is believed to be novel, one skilled in the art may also synthesize photosensitizer E and other photosensitizers of the present invention. (See, e.g., Sethna Chem. Rev., 36:10 (1945); Sethna et al. Organic Reactions, 7:1 (1953)).

The following examples are presented in order to help define and enable the present invention. The examples are not to be considered as limiting the invention as described and claimed herein.

EXAMPLES

Example 1

Inactivation of HIV-1Virus in Platelet Concentrate.

The experimental design for the viral validation studies involved the addition of photosensitizer B to platelet concentrates in standard platelet collection bags and subsequent activation of the photosensitizer upon exposure to ultraviolet light at 320–400 nm. The following studies were performed for the validation of elimination of HIV-1 from platelet concentrates.

Photosensitizer Toxicity Test (PHASE 1): This study was performed to establish the degree of toxicity of the photosensitizer to the indicator cell lines used in the assay and to rule out any interference by the photosensitizer with the ability of the chosen viruses to infect the indicator cell lines.

PHASE I: Photosensitizer Toxicity to Viral Indicator Cells
Sample Set #1
1. Platelet+Saline+Orbital Shaking+30 min ambient light.
2. Platelet+Saline+Orbital Shaking+30 min UVA.
3. Platelet+100 µg/mL Photosensitizer B+Orbital shaking+30 min ambient.
4. Platelet+100 µg/mL Photosensitizer B+Orbital Shaking+30 min UVA.
5. Platelet+300 µg/mL Photosensitizer B+Orbital Shaking+30 min ambient.
6. Platelet+300 µg/mL Photosensitizer B+Orbital Shaking+30 min UVA.

Sample Set #2
7. Platelet+Saline+Orbital Shaking+60 min ambient light.
8. Platelet+Saline+Orbital Shaking+60 min WVA.
9. Platelet+100 µg/mL Photosensitizer B+Orbital Shaking+60 min ambient light.
10. Platelet+100 µg/mL Photosensitizer B+Orbital Shaking+60 min UVA.
11. Platelet+300 µg/mL Photosensitizer B+Orbital Shaking+60 min ambient light.
12. Platelet+300 µg/mL Photosensitizer B+Orbital Shaking+60 min UVA.

PHASE II
Photosensitizer Dose Response: The main purpose of this study was to determine the optimum concentration of photosensitizer for complete inactivation of HIV-1.
Kinetics of Inactivation: The main purpose of this study was to establish the optimal exposure time for effective inactivation of HIV-1.

Variables Under Investigation
1. Dose of Photosensitizer (Dose response studies).
2. UVA Exposure time (Kinetics of inactivation).

Fixed Parameters
1. Light Source (UVA)
2. Photosensitizer-B
3. Virus-HIV-1.
4. Suspending medium (Plasma)
5. Light intensity (including distance of sample from the light source).
6. Rotational speed for sample platform.
7. Viral Titer ($2\times10^7$).
8. Post-Photosensitizer incubation time (10 minutes).
9. UVA Reactor (Orbital shaker)

PHASE III: Elimination of HIV in Platelet Concentrates—EXPERIMENTAL CONDITIONS
Dose Response
Kinetics of Inactivation
Sample Set #1
13. Platelet+Virus+Saline+Orbital Shaking+5 min ambient light.
14. Platelet+Virus+Saline+Orbital Shaking+5 min UVA.
15. Platelet+Virus+50 µg/mL Photosensitizer B+Orbital Shaking+5 min UVA.
16. Platelet+Virus+100 µg/mL Photosensitizer B+Orbital Shaking+5 min UVA.
17. Platelet+Virus+200 µg/mL Photosensitizer B+Orbital Shaking+5 min UVA.
18. Platelet+Virus+300 µg/mL Photosensitizer B+Orbital Shaking+5 min UVA.
18A. Platelet+Virus+400 µg/mL Photosensitizer B+orbital Shaking+5 min UVA.

Sample Set #2
19. Platelet+Virus+Saline+Orbital Shaking+5 min ambient light.
20. Platelet+Virus+Saline+Orbital Shaking+5 min UVA.
21. Platelet+Virus+50 µg/mL Photosensitizer B+Orbital Shaking+5 min UVA.
22. Platelet+Virus+100 µg/mL Photosensitizer B+Orbital Shaking+5 min UVA.
23. Platelet+Virus+200 µg/mL Photosensitizer B +Orbital Shaking+5 min UVA.
24. Platelet+Virus+300 µg/mL Photosensitizer B+Orbital Shaking+5 min UVA.
24A. Platelet+Virus+400 µg/mL Photosensitizer B+Orbital Shaking+5 min UVA.

Sample Set #3
25. Platelet+Virus+Saline+Orbital Shaking+30 min ambient light.
26. Platelet+Virus+Saline+Orbital Shaking+30 min UVA.
27. Platelet+Virus+50 µg/mL Photosensitizer B+Orbital Shaking+30 min ambient.
28. Platelet+Virus+50 µg/mL Photosensitizer B+Orbital Shaking+30 min UVA.
29. Platelet+Virus+100 µg/mL Photosensitizer B+Orbital Shaking+30 min ambient.
30. Platelet+Virus+100 µg/mL Photosensitizer B+Orbital Shaking+30 min UVA.
31. Platelet+Virus+200 µg/mL Photosensitizer B+Orbital Shaking+30 min ambient.
32. Platelet+Virus+200 µg/mL Photosensitizer B+Orbital Shaking+30 min UVA.
33. Platelet+Virus+300 µg/mL Photosensitizer B+Orbital Shaking+30 min ambient.
34. Platelet+Virus+300 µg/mL Photosensitizer B+Orbital Shaking+30 min UVA.
34A. Platelet+Virus+300 µg/mL Photosensitizer B+Orbital Shaking+30 min UVA.

Sample Set #4
35. Platelet+Virus+Saline+Orbital Shaking+60 min ambient light.
36. Platelet+Virus+Saline+Orbital Shaking+60 min UVA.
37. Platelet+Virus+50 µg/mL Photosensitizer B+Orbital Shaking+60 min ambient.
38. Platelet+Virus+50 µg/mL Photosensitizer B+Orbital Shaking+60 min UVA.
39. Platelet+Virus+100 µg/mL Photosensitizer B+Orbital Shaking+60 min ambient.
40. Platelet+Virus+100 µg/mL Photosensitizer B+Orbital Shaking+60 min UVA.
41. Platelet+Virus+200 µg/mL Photosensitizer B+Orbital Shaking+60 min ambient.
42. Platelet+Virus+200 µg/mL Photosensitizer B+Orbital Shaking+60 min UVA.
43. Platelet+Virus+300 µg/mL Photosensitizer B+Orbital Shaking+60 min ambient.

44. Platelet+Virus+300 µg/mL Photosensitizer B+Orbital Shaking+60 min UVA.

Note: Ambient means ambient laboratory light (Non-WVA light Source).

METHODS—PHASE I:

I. Selection of uniform UVA exposure area:

Step 1: Place a transparent sample platform at equidistant from the top and bottom UVA lamps.

Step 2: Construct a square on the sample platform of the reactor.

Step 3: Switch on the top-bank of UVA light and turn on the fan for maintenance of ambient temperature during photolysis.

Step 4: Place the light intensity meter at both the four corners of the square and the center. Record the light intensity meter readings at these locations for the top bank of lights.

Step 5: Repeat step 4 for the bottom bank of lights.

Step 6: If the light intensity is different for the various locations, reconstruct the "square" such that light intensity is the same at all the different sections of the square.

Step 7: Preparation of Stock Solution Photosensitizer B: Dissolve Photosensitizer B in 10 mM of phosphate buffered saline 9PBS) such that the final concentration is 40 mg/mL, solution A. Prepare the following working solutions from solution A:
 1. Solution B: 5 mg/mL
 2. Solution C: 10 mg/mL
 3. Solution D: 20 mg/mL
 4. Solution E: 30 mg/mL Preparation of Platelet Concentrates for UVA Irradiation Step 8: Pool four units of ABO compatible platelet concentrates together in a standard platelet collection bag to obtain a final volume of about 182 mL of platelet rich plasma (Plate let Suspension F). Place 50 mL of platelet concentrates into standard platelet collection bag for experiment in Phase 1A (Platelet Suspension G). Save the remaining 132 mL of platelet concentrates for Phase II studies.

Step 9: Samples 1–12: Place 7.0 mL aliquots of suspension G into 15 mL centrifuge tubes labeled for both control and test samples (100 and 300 µg/mL).

Step 10: Pipette 71 µl of working solutions C and E and add to platelet concentrates (from step 8) and allow samples to incubate with photosensitizer at 24° C. for 10 minutes at ambient light. Add 71 µl of phosphate buffered saline (PBS) to control samples and incubate as described above.

Step 11: Place 3.0 mL aliquots of treated and untreated samples from Step 10 in 35 mm petridishes. Place plastic covers on top of the petridishes and irradiate samples according to the experimental conditions that are outlined for Phase 1A studies.

Step 12: At the end of the appropriate irradiation period, pour platelet samples into 5 mL test tubes. Test control and treated samples for (1) cellular toxicity for viral assay system; (2) viral interference for assay system.

METHODS-PHASE II:

1. Selection of uniform UVA exposure area: Use the same area of uniform light distribution as in Phase I studies (i.e., Steps 1–6 are the same).

Step 7: Preparation of Stock Solution B: (Same as in Phase I).

Preparation of Platelet Concentrates with HIV-1. for UWA Irradiation

Step 8: Add 8 mL of HIV-1 ($2\times10^7$ PFU of HIV-1/mL) to the remaining 132 mL of platelet concentrates (from step 8 of Phase I) such that the final HIV-1 titre is about $1.1\times10^6$ (Platelet-HIV Suspension H). Divide platelet suspension H into the following aliquots for the different sample sets in the Phase II viral elimination studies:
 1. 27 mL of Suspension H for Sample Set #1
 2. 27 mL of Suspension H for Sample Set #2
 3. 39 mL of Suspension H for Sample Set #3
 4. 39 mL of Suspension H for Sample Set #4

Step 9: Prepare samples for viral elimination studies.

Step 10: Place 3.0 mL aliquots of treated and untreated samples from Step 4 into 35 mm petridishes. Place plastic covers on top of the petridishes and irradiate samples according to the experimental conditions that are outlined above.

Step 11: At the end of the appropriate irradiation period, pour platelet samples into 5 mL test tubes. Determine HIV-1 infectivity in control and treated samples.

HIV Infectivity Assay:

HIV is normally titrated in vitro by a MT-4 syncytium assay. MT-4 is a cell line developed specifically to facilitate the recognition of HIV infection. These cells are adherent and abundantly express the CD4 receptor used by HIV during infection of a cell. Upon infection with HIV, these cells develop easily-detectable multinucleated cells or syncytium forming units.

Buffer Toxicity/Viral Interference

Twenty-four well cluster plates were seeded with MT-4 cells in a total volume of 1.0 ml/well. Each test dilution was inoculated into 3 wells at 0.1 ml/well, then the cultures were incubated at 36° C.±1° C. Observations for cytotoxicity and, if necessary, an estimation of the percentage of cells affected in each culture were performed on day 5 and day 7 post-inoculation.

Viral Inactivation Assay

The test article samples were spiked with human immunodeficiency virus type 1. The spiked test article samples were carried through the inactivation process. All samples were tested undiluted or diluted in RPMI medium (negative control) at various dilutions. Retained samples were stored frozen at −60° C. or below.

Titration of Samples for the Presence of HIV-1

Twenty-four well cluster plates were seeded with MT-4 cells in a total volume of 1.0 ml/well. From the spiked test article or positive control, ten fold serial dilutions were made in culture medium. At each dilution step quadruplicate 0.1 ml volume of the samples were tested. Cultures were fed twice a week by removal of 1.0 ml of medium and addition of 1.0 ml of fresh medium. On days 7, 14 and 28 the cultures were evaluated for the cytopathic effects to determine the $TCID_{50}$. On days 7, 14 and 28, 1.0 ml of each culture was removed for analysis by HIV-1 p24 antigen capture ELISA.

The formula for the final titer calculation of $TCID_{50}$ is based on the Karber method: negative logarithm of the endpoint titer=A−($S_1$/100−0.5)−B, where A=negative logarithm of the highest concentration inoculated, $S_1$=sum of the percentage positive at each dilution, and B=$\log_{10}$ (of the dilution factor). The values were converted to $TCID_{50}$/ml using a sample inoculum volume of 0.1 ml.

The p24 assay is the Coulter HIV p24 Ag Assay which is an enzyme immunoassay for the detection of p24 antigen of HIV in plasma, serum or tissue culture media. It uses a murine monoclonal antibody (anti-HIV core antigen) coated onto microwell strips and if present the antigen binds to the antibody-coated microwells. The bound antigen is recognized by biotinylated antibodies to HIV which react with conjugated streptavidin horseradish peroxidase. Color develops from the reaction of the peroxidase with hydrogen peroxide in the presence of tetramethylbenzidine substrate. The intensity of the color developed is directly proportional to the amount of HIV antigen present in the sample. The p24 assay negative control was RPMI 1640 and the positive control was antigen reagent.

Culture fluid from each well is analyzed by the HIV p24 assay and the absorbance value is compared to the cut off value for a positive result. The cut off value for a positive result was determined by adding the mean absorbance value of the ELISA negative control to a predetermined factor of 0.055. The expected range of the cut off value is 0.055 to 0.155. If the absorbance value for the well exceeds the cut off value, then the well is considered positive for HIV p24 antigen. The level of HIV p24 in each well is not quantitated. The $TCID_{50}$ of the sample was determined from the sum of the percentage of wells positive for HIV p24 antigen at each dilution using the standard formula stated above.

| Materials | |
|---|---|
| Positive Control Article and Spiking Virus: | Human immunodeficiency virus type 1<br>Strain: IIIB<br>Lot No.: VP012 H.1/8/93<br>Titer = $10^{7.5}$ $TCID_{50}$/ml<br>Source: Advanced Biotechnologies, Inc.<br>Columbia, Maryland |
| Negative Control Article: | RPMI 1640 Medium<br>Source: Microbiological Associates, Inc.<br>Rockville, Maryland |
| Test System: | MT-4 cells (L013-T)<br>Source: National Institute of Health<br>Bethesda, Maryland<br>(Human T cells isolated from a patient with adult T cell leukemia; HTLV-I transformed) |

Results

Cytotoxicity was observed with all the undiluted samples, however the cultures appeared to recover from the effects by day 7. Cytotoxicity was observed with all the samples diluted 1:10 on day 3, however the cultures recovered by day 7. These effects were most likely due to the excessive amount of cellular material in the samples.

Results for samples taken at various points during the inactivation of HIV-1 study were obtained. The following samples showed no evidence of replication competent HIV-1: 34A, 42 and 44. One well of four inoculated with undiluted sample 34 and sample 32 was positive for CPE on day 28. Two wells of four inoculated with undiluted sample 40 were positive for CPE on day 28. The remaining samples had significant levels of replicating HIV-1.

Example 2

Inactivation of Sindbis in Plasma Solution.

Human plasma was spiked with Sindbis virus to a final concentration of >7 $log_{10}$ plaque forming units (PFU)/mL. Photosensitizer was then added to a virus spiked plasma at 100 or 300 ug/mL final concentration. After a 15 minute incubation at room temperature samples of photosensitizer treated virus spiked plasma was placed in a ultraviolet light (UV) irradiator and exposed to 24 $J/cm^2$ of UVA energy. Treated samples were then assayed for residual infectious virus by plaque assay. Virus reduction ($V_R$) was calculated by the equation $V_s - V_f = V_R$ where $V_s$ is the starting virus titer, and $V_f$ is the virus titer after treatment.

Example 3

Inactivation of Cytomegalovirus in Human Platelet Concentrates.

Inactivation of Cytomegalovirus (CMV) in human in platelet concentrates was conducted under normal ambient oxygen tension using a photosensitizer and long wavelength ultraviolet light (UVA) at 22±20° C. Dose response and kinetics studies were conducted in order to determine the optimal conditions for inactivation of CMV in human platelet. 4–6 logs of CMV virus was added to standard units of human platelet concentrate. The contaminated platelet concentrates were incubated at ambient non-UVA laboratory light for 60±5 minutes with different concentrations of CP-38 (100–300 µg/mL). Following incubation, the platelet concentrates were exposed to UVA at different fluences (14–43 $J/cm^2$). Inactivation of CMV virus was evaluated by an infectivity assay using MRC-5 cells. Complete inactivation of CMV was obtained at 100 µg/mL using Photosensitizer B and a UVA fluence of 21.6 $J/cm^2$.

Example 4

Inactivation of Vesicular Stomatitis Virus in Platelet Concentrates.

Inactivation of Vesicular Stomatitis (VSV) in human platelet concentrates was conducted under normal ambient oxygen tension using a photosensitizer and long wavelength ultraviolet light (UVA) at 22+2° C. Dose response and kinetics studies were conducted in order to determine the optimal conditions for inactivation of VSV in human platelet. 6 logs of VSV virus was added to standard units of human platelet concentrate. The contaminated platelet concentrates were incubated at ambient non-UVA laboratory light for 10+5 minutes with different concentrations of photosensitizer B (30 and 150 µg/mL). Following incubation, the platelet concentrates were exposed to UVA at different fluences (4.20–8.40 $J/cm^2$). Inactivation of VSV virus was evaluated by an infectivity assay (plaque assay) using Vero cells. Inactivation of 6 logs of VSV using Photosensitizer B was obtained at a minimum UVA fluence of 4.20 $J/cm^2$.

Example 5

Inactivation of Herpes Simplex Virus Type 1 in Calf Serum.

Inactivation of Herpes Simplex Virus type 1 (HSV-1) in calf serum was conducted under normal ambient oxygen tension using a photosensitizer and long wavelength ultraviolet light (UVA) at 22+2° C. Using a fixed concentration of Photosensitizer B (30 µg/mL) kinetics studies were conducted in order to determine the optimal conditions for inactivation of HSV-1 in calf serum. 3 logs of HSV-1 virus was added to 100 mL of calf serum. The contaminated sera were incubated at ambient non-UVA laboratory light for 10±5 minutes. Following incubation, the sera were exposed to UVA at different fluences (4.20–8.40 $J/cm^2$). Inactivation of HSV virus was evaluated by an infectivity assay. Inactivation of 3 logs of HSV-1 using Photosensitizer B was obtained at a UVA fluence of 12.6 J/cm$^2$.

Example 6

Measurement of Photosensitizer Mutagenicity by Ames Mutagenicity Test.

The Ames test is based upon the use of five specially constructed strains of Salmonella typhimurium containing a specific mutation in the histidine operon. These genetically altered strains, TA98, TA100, TA1535, TA1537, and TA1538 cannot grow in the absence of histidine. When they are placed in a histidine-free medium, only those cells which mutate spontaneously back to their wild type state (non-histidine-dependent by manufacturing their own histidine) are able to form colonies. The spontaneous mutation rate (or reversion rate) for any one strain is relatively constant, but if a mutagen is added to the test system, the mutation rate is significantly increased. Each tester strain contains, in addition to a mutation in the histidine operon, two additional mutations that enhance sensitivity to some mutagens. The rfa mutation results in a cell wall deficiency that increases the permeability of the cell to certain classes of chemicals such as those containing large ring systems that would otherwise be excluded. The second mutation is a deletion in the uvrB gene resulting in a deficient DNA excision-repair system. Tester strains TA98 and TA100 also contain the pKM101 plasmid (carrying the R-factor). It has been suggested that the plasmid increases sensitivity to mutagens by modifying an existing bacterial DNA repair polymerase complex involved with the mismatch-repair process. TA98, TA1537 and TA1538 are reverted from histidine dependence (auxotrophy) to histidine independence (prototrophy) by frameshift mutagens. TA100 is reverted by both frameshift and base substitution mutagens and TA1535 is reverted only by mutagens that cause base substitutions.

EXPERIMENTAL DESIGN FOR AMES MUTAGENICITY TEST

The experiment was designed such that the concentrations of Photosensitizer B on the agar plate is equivalent to the expected final dose in a recipient given 5 units of platelet concentrates. Note that 5 units of platelet concentrates is equivalent to a standard single therapeutic (1TD). Calculation of the theoretical concentration of photosensitizer B is based on the following deductions assuming homogenous distribution of the drug in a 70 kg normal individual:

| | |
|---|---|
| 1. Normal Blood Volume = | 5600 mL |
| 2. 1 Unit of Platelet Concentrate = | 50 mL |
| 3. 1 Therapeutic Dose (1TD) = | 5 Units of Platelet Concentrates |
| 4. Volume of 1TD = | 250 mL |
| 5. Starting Concentration of Photo-Sensitizer B = | 300 µg/mL |
| 6. Irradiation for sufficient time to break down 90% of Photosensitizer B | |

Based on the above assumptions, if a patient receives 5 Units of platelet concentrates the final concentration of Photosensitizer B in the body is derived as follows:

$$
\begin{aligned}
7.\ \text{Final Body Concentration of Photosensitizer} &= \frac{300\ \mu g/mL \times \text{Total Vol. of Platelets}}{\text{Total Blood Volume}} \\
&= \frac{300\ \mu g/mL \times 250}{5580} \\
&= 12.8\ \mu g/mL\ \text{of Photosensitizer}
\end{aligned}
$$

10% Residual photo-sensitizer $B$ after UVA irradiation = 1.28 µg/mL of Photosensitizer A Salmonella/mammalian microsome mutagenicity test was conducted to determine whether a plasma test article solution of Photosensitizer B in platelet concentrates would cause mutagenic changes in histidine-dependent mutant strains of Salmonella typhimurium. The Ames mutagenicity test system has been widely used as a rapid screening procedure for the determination of mutagenic and potential carcinogenic hazards of pure compounds, complex compounds and commercial products.

Example 7

Measurement of Photosensitizer Cytotoxicity using Mouse Fibroblasts.

In vitro mammalian cell culture studies have been used historically to evaluate the cytotoxicity of biomaterials and complex chemical compounds. Mouse fibroblasts (L-929) were grown to confluency in 25 cm$^2$ culture flasks using sterile minimum essential medium (MEM) supplemented with 5% fetal calf serum and nontoxic concentrations of penicillin, streptomycin and amphotericin B. Confluent monolayers of L-929 cells were exposed to extract dilutions of Photosensitizer B. A standard Solution of Photosensitizer B was prepared by dissolving 12 mg in 20 mL of MEM supplemented with 5% bovine serum and then incubated at 37° C. for 24 hours. Following incubation, different dilutions (1:2 to 1:16) of standard stock of Photosensitizer B were prepared with fresh MEM. A 5 mL aliquot of the different dilutions of Photosensitizer B was added to confluent monolayers of L-929 cells and then incubated at 37° C. for 72 hours. A 5 mL MEM aliquot was added as a negative control. After exposure to Photosensitizer B, the cells were examined microscopically at approximately 100× and scored for cytotoxic effects (CTE) at the end of the 24, 28 and 72 hours of incubation. Presence (+) or absence (−) of a confluent monolayer, vacuolization, cellular swelling and the percentage of cellular lysis were also recorded. CTE was scored as either Nontoxic (N), Intermediate (I) or Toxic (T). These data are shown in Table 2. The evaluation criteria are shown below:

| CTE SCORE | MICROSCOPIC APPEARANCE OF CELLS |
|---|---|
| Nontoxic (N) | A uniform confluent monolayer with primarily elongated cells, with discrete intracytoplasmic granules present at the 24 hour observation. At the 48 and 72 hour observation periods, there should be an increasing number of rounded cells as cell population increases and crowding begins. Little or not vacuolization, crenation or swelling should be present. |

| CTE SCORE | MICROSCOPIC APPEARANCE OF CELLS |
|---|---|
| Intermediate (I) | Cells may show marked vacuolization, crenation or swelling. Cytolysis (0–50%) of cells that results in "floating" cells and debris in the medium may be present. The remaining cells are still attached to the flask. |
| Toxic (T) | Greater than 50% of all cells have been lysed. Extensive vacuolization, swelling, or crenation are usually present in the cells remaining on the flask surface. |

Example 8

Measurement of Photosensitizer Cytotoxicity using Chinese Hamster Ovary (CHO) Hybridoma Cells and AE-L Cells Chinese hamster ovary, and AE-L cells were grown to confluency in 25 cm$^2$ culture flasks using sterile Eagles Minimum Essential Medium (EMEM) supplemented with 2 mM L-glutamine, 1% Proline, 5% calf serum treated with different concentrations of Photosensitizer B (30–150 µg/mL) in the presence of UVA. Nontoxic concentrations of penicillin, streptomycin and amphoteric B were also added to the culture medium to prevent bacterial growth. Control samples contained nontreated calf serum. All samples were incubated at 37° C. for 2 to 7 days. The number of viable cells were measured at the end of the incubation periods. Results show that the growth and viability of the two cell types were not affected by pretreatment of the sera with irradiated and non-irradiated Photosensitizer B. The viability of CHO cells as well as the expression of rhCg proteins on recombinant CHO cell lines were not affected. Note that upon UVA exposure of 30 minutes in the presence of 30 µg/mL of Photosensitizer B, there were no adverse effects with the growth supporting functions of the treated sera or the expression of rhCg antigens.

Example 9

Synthesis of 3-Bromo-7-(γ-Triethylammonium Propyloxy) Coumarin Bromide (Photosensitizer A).

Into a 1000 mL round bottom flask containing a 2.5 cm stirring bar was added 15 g of 7-hydroxycoumarin, 15 g of potassium carbonate, 500 mL of tetrahydrofuran (THF) and 70 mL of 1,3-dibromopropane. After stirring at reflux for 3–4 days (72–96 hours), the solution was filtered, the solids washed 4 times with 50 mL of dichloromethane and the combined filtrate concentrated by rotary evaporator. 50 mL of ethyl acetate was added to the concentrate followed by concentration under reduced pressure (25 in Hg.). Another 50 mL of ethyl acetate was added to the concentrate followed by filtration. The solids were washed 3 times with 10 mL of a 1:1 mixture of ethyl acetate and hexane. After drying, 15–20 g of the crude product was dissolved in 150–200 mL of dichloromethane and purified by flash chromatography (130–150 g SiO$_2$ (70–230 mesh), 35 mm O.D. column, approximately 60 cm in length), using dichloromethane as the eluting solvent. The fractions were collected in 50–250 mL beakers and monitored by TLC (developing solvent: 4:6 mixture of ethyl acetate:hexane). The fractions containing product were combined, concentrated by rotary evaporator and dried.

Synthesis of 3-bromo-7-(γ-bromopropyloxy)coumarin.

Into a 500 mL round bottom flask containing a 2.5 cm stirring bar was added 13 g of 7-(γ-bromopropyloxy) coumarin and 120–150 mL of THF. When the 7-(γ-bromopropyloxy)coumarin was completely dissolved, 3 mL of bromine was added by syringe. After stirring for 2–5 hours at room temperature, the solution was concentrated by rotary evaporator. 50 mL of a 1:1 mixture of ethyl acetate and hexane was added to the concentrate and the mixture was stirred for 30 minutes at room temperature. The solution was then filtered and the solids washed 3 times with 1:1 ethyl acetate and hexane and then dried for 2 hours. To obtain additional product, the filtrate was concentrated by rotary evaporator and 30 mL of a 1:1 mixture of ethyl acetate and hexane was added to the concentrate. The resulting mixture was then filtered, the solids washed three times with 1:1 ethyl acetate and hexane and then dried for 2–5 hours. The product was checked by TLC (ethyl acetate:hexane (4:6)).

The crude product (13–16 g) was dissolved in 100–170 mL of dichloromethane and purified by flash chromatography (100–150 g SiO$_2$ (70–230 mesh), 35 mm O.D. column, approximately 60 cm in length), using dichloromethane as the eluting solvent. Fractions were collected in a 50–250 mL beakers and monitored by TLC (developing solvent: ethyl acetate:hexane (4:6)). The fractions containing product were combined, concentrated by rotary evaporator and dried.

Synthesis of 3-bromo-7-(γ-triethylammoniumpropyloxy) coumarin bromide.

Into a 500 mL round bottom flask containing a 2.5 cm stirring bar was added 11 g of 3-bromo-7-(γ-bromopropyloxy)coumarin, 150–200 mL of THF and 60–70 mL of triethylamine. After stirring at reflux for 3–4 days (72–96 hours), the solution was filtered and the solids washed 3 times with 10 mL of acetone, 3 times with 10 mL of hexane and then dried for 1 hour. The product was transferred to a 600 mL beaker and 80 mL of acetone was added. The mixture was stirred for 30 minutes, filtered, washed 3 times with 10 mL of acetone and dried for 3–5 hours. The product was checked by TLC (ethyl acetate:hexane (4:6)).

Figure 10:
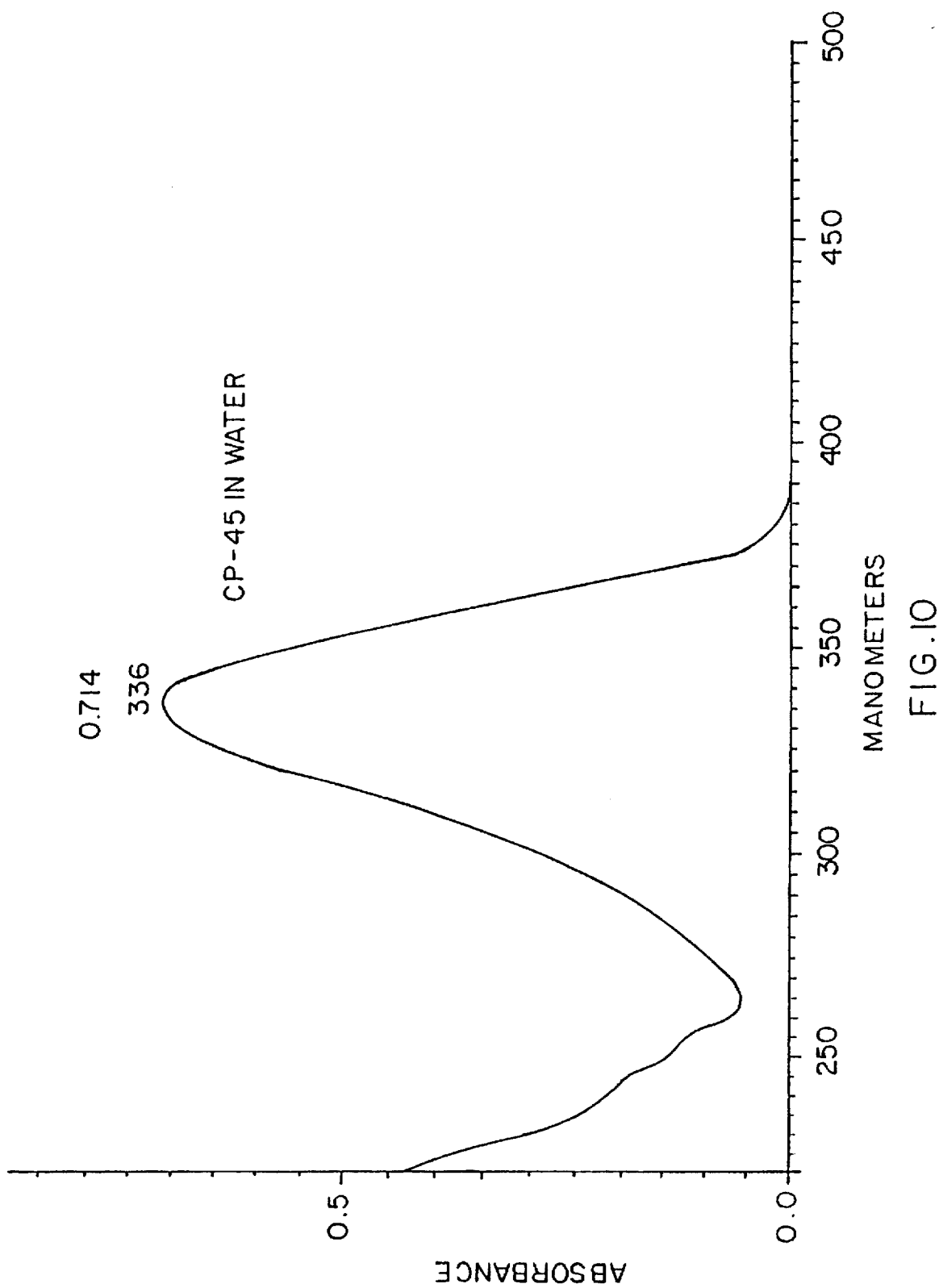
FIG. 10 depicts the absorption spectrum of photosensitizer A.
Figure 11:
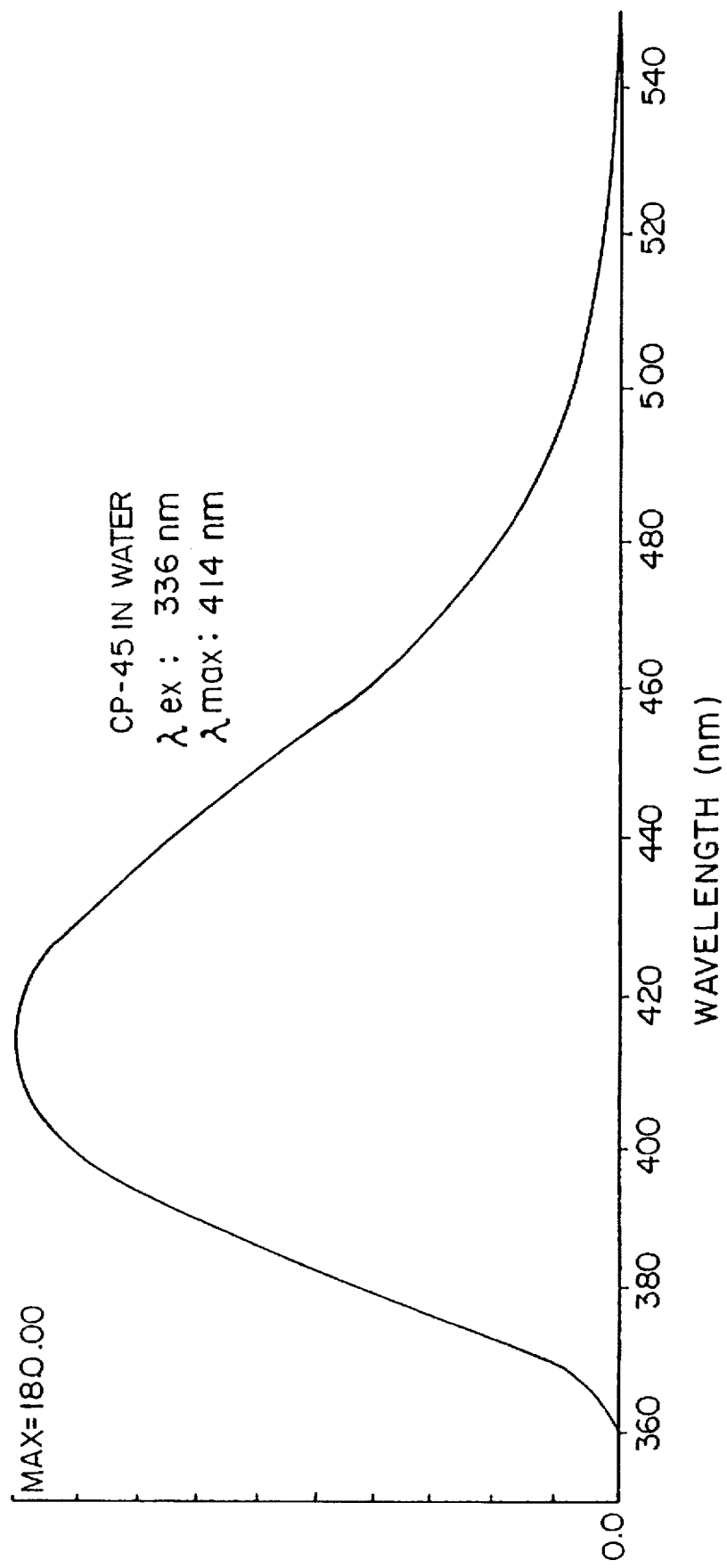
FIG. 11 depicts the fluorescence spectrum of photosensitizer A.

Photosensitizer A was found to fluoresce when irradiated with U.V. light. The absorption spectrum of photosensitizer A in water is shown in FIG. 10. The fluorescence spectrum of photosensitizer A is shown in FIG. 11.

Example 10

Measurement of Photosensitizer Migration in Solution.

Dialysis experiments were carried out using a custom-made polystyrene dialysis chamber. The unit consists of three chambers capable of holding a volume of 10 mL of solution. Each chamber was separated from the adjoining chamber by a dialysis membrane (MW cut off, 5000, Fisher). The center chamber was loaded with 100 µM photosensitizer solution either in phosphate buffered saline (PBS) or plasma. The other two adjoining chambers were loaded with solutions containing the agents for which the binding was to be tested. Liposomes were prepared by vertexing dioleyl phosphatidylserine (4.0 mg/mL, Avanti polar lipids) solution in PBS. Polyadynelic acid (Poly A; Sigma), Calf thymus DNA (DNA; Sigma) and bovine serum albumin (BSA) solutions were prepared in PBS (4.0 mg/mL). The dialysis cells containing solutions were allowed to equilibrate with constant agitation for a period of 24 hours at room temperature. At the end of 24 hours, the solutions were removed from individual chambers and absorbance was determined at 350 nm using a spectrophotometer. For experiments involving liposomes, 5% Titron X-100 (Sigma) was used to clarify the solutions prior to absorbance reading. Quantitative determination of photosensitizer in plasma and platelets was carried out by high performance liquid chromatography (HPLC) equipped with a C18 reverse phase column.

Example 11

Irradiation of Platelet Concentrates and Photosensitizen.

Random donor platelet concentrates (24 hours old) were obtained from American Associate of Blood Banks accredited blood banks. Platelet units were aseptically pooled and subsequently split into controls and treatments. 10 mL of photosensitizer solution in 0.9% saline was added to 50 mL platelet concentrates in CLX (Miles) containers to obtain the photosensitizer final preset concentration. After addition of the photosensitizer the platelet units were incubated at room temperature while mixing on a shaker for 10 minutes. Platelet concentrates containing photosensitizers were UVA irradiated from top and bottom in a prototype UVA reactor to deliver 25 J/cm$^2$ fluence. During the irradiation, samples were placed on a linear shaker. After UVA exposure the samples were stored in a platelet incubator with shaking for an additional 4 days. During storage 3 mL aliquots from each unit were collected and subsequently analyzed for platelet in vitro properties.

Example 12

Compsrison Study of Photosensitizer B, 8-MOP, and AMT.

Full units of one day old human platelet concentrates were collected in Cyrocyte bags (PL 269, Fenwal, Deerfield, Ill.) according to standard blood banking procedures (AABB Technical Manual, pg. 136, 13th Ed. 1989). Platelet units were spiked with 6 logs of bacteriophage φ6. Equimolar concentrations (60 μM) of 8-MOP, AMT and brominated psoralen were added to the platelet concentrations and then incubated at 22±2° C. for 10 minutes. Treated samples were irradiated from top and bottom with a constant total ultraviolet-A light source intensity of 7 mW/cm$^2$. During UVA exposure samples were continuously agitated to ensure adequate mixing. Virucidal properties were evaluated using a standard double agar plaque assay consisting of host bacteria *Pseudomonas Syringe*. In vitro platelet properties were evaluated using (1) aggregation response to collagen; (2) hypotonic shock response; (3) morphology according to method described by Kunicki, et al. (Transfusion 15:414–421, 1975). Data represents the mean+standard deviation of n=3.

Example 13

Comparison Study of Photoinactivation of Sindbis Virus in Human Plasma.

A comparison study was performed to evaluate the viral inactivation properties of photosensitizers A, B, D, and E of the present invention. Also examined were non-halo genated forms of photosensitizer A (hereinafter referred to as photosensitizer AX), photosensitizer C (hereinafter referred to as photosensitizer CX), and photosensitizer D and E (hereinafter referred to as photosensitizer DX). The TCID50 assay was used to measure the affects of virus inactivation.

Figure 12:
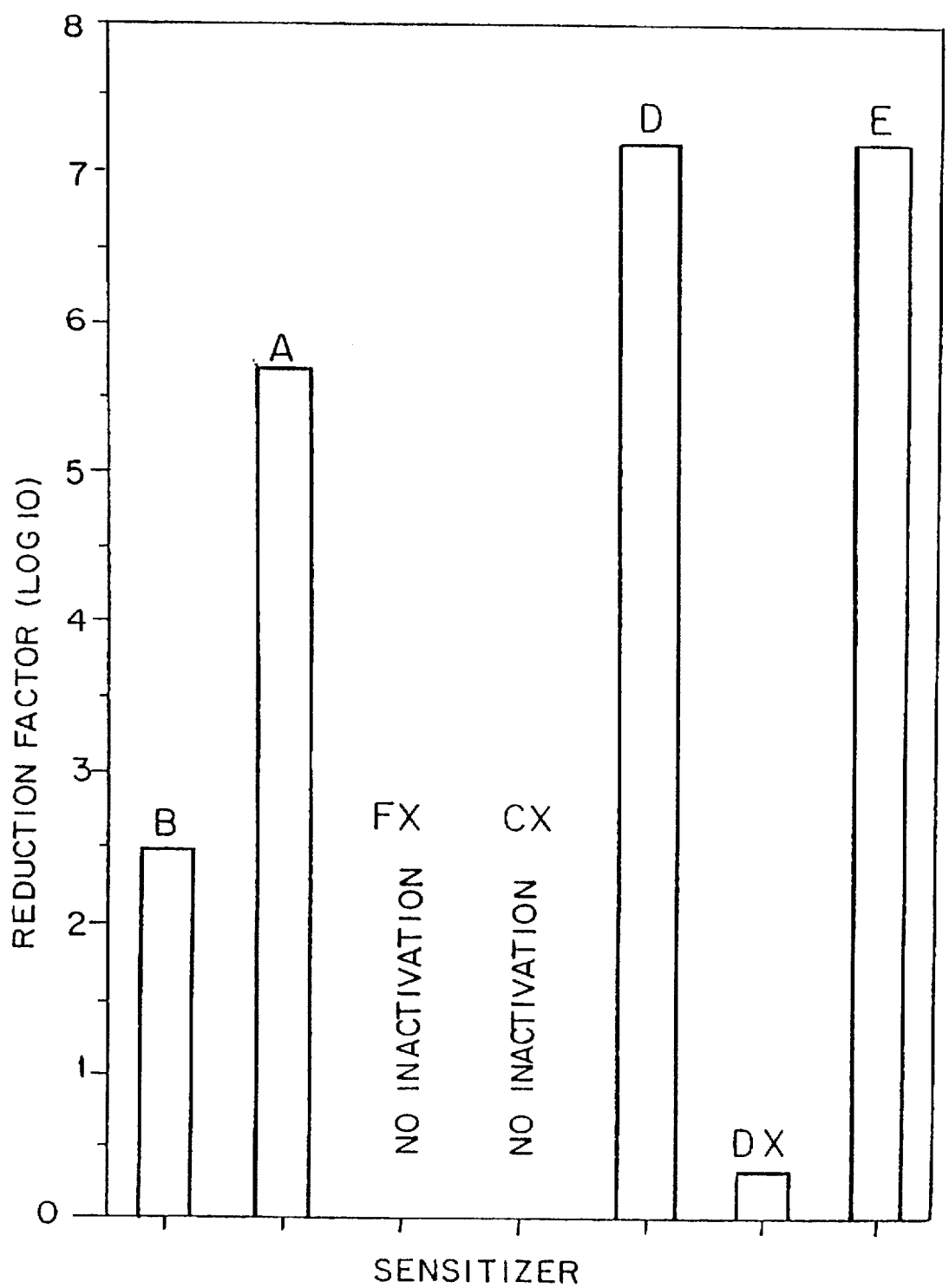
FIG. 12 depicts the inactivation of Sindbis virus with photosensitizers B, A, AX, CX, D, DX and E.

The photosensitizer was added to virus spiked plasma. The virus employed was Sindbis and the plasma was spiked to a working titer of $>1\times10^7$. Each test unit was exposed to ultraviolet light at 320–400 nm (peak absorbance 365 nm) for 30 min. to achieve an irradiation of about 24 J/cm$^2$. Virus inactivation was quantitated by plaque assay. A monolayer of indicator cells were grown on a solid support and exposed to sample materials to allow for virus attachment. A foci of infection develops as virus replicate, lyse and released virus diffuses to, and infects, neighboring cells or virus infects neighboring cells via cell-cell fusion. CPE develops after several days of incubation. The virus titer in the sample is calculated from number of units exhibiting CPE. The results of this experiment are shown in FIG. 12.

Example 14

Synthesis of 3-Bromo-7-(γ-Triethylammonium Propyloxy) Coumarin (Photosensitizer D).

Preparation of 7-hydroxy-8-methyl coumarin. 2-methyl resorcinol (0.161 mmol, 20.024 g) and malic acid (0.165 mmol, 22.129 g) were dissolved in concentrated sulfuric acid. The reaction mixture was stirred at 80° C. for 24 h. The resulting solution was then poured over crushed ice, and the precipitate was collected by vacuum filtration. The precipitate was then washed with 5% NaHCO$_3$ and again collected by vacuum filtration yielding an orange-yellow solid in a 20.64% yield.

Preparation of 7-3'-bromopropyloxy-8-methyl coumarin. 7-hydroxy-8-methyl coumarin (0.286 mol, 5.045 g) and K$_2$CO$_3$ (0.0317 mol, 4.379 g) were added to 50 ml of dibromopropane. The reaction was stirred at reflux for 24h. The excess dibromopropane was removed by distillation. The remaining slurry was taken up in CHCl$_3$ and gravity filtered to remove the K$_2$CO$_3$. The CHCl$_3$ was dried and removed in vacuo. The final solid was washed with hexanes to give a pale-yellow product in a 76.0% yield.

Preparation of 3 bromo-7-3'-bromopropyloxy-8-methyl coumarin. 7-3'-bromopropyloxy-8-methyl coumarin (6.75 mmol, 2.01 g) was dissolved in THF and cooled to –76° C. Approximately 3 ml of Br$_2$ was slowly added to the solution. The mixture was stirred for 3 h and then allowed to warm to room temperature. The resulting solution was dissolved in CHCl$_3$ and washed with a 10% Na$_2$S$_2$O$_4$ solution, a 10% NaHCO$_3$ solution and finally water. The CHCl$_3$ was dried and removed in vacuo. The resulting pale-yellow solid was washed with hexanes and collected by vacuum filtration to give a quantitative yield.

Preparation of 3-bromo-7-(γ-triethylamino-propyloxy)-8-methyl coumarin. 7-3'-bromopropyloxy-8-methyl coumarin (0.17 mmol, 0.064 g) was dissolved in 30 ml of CHCl$_3$. Approximately 10 ml of triethylamine was added to the solution. By following TLC, the reaction required refluxing for 48 h to ensure completion. The CHCl$_3$ and Et$_3$N were removed in vacuo. The precipitate was washed with hexane, ethyl acetate and acetone several times. The resulting white solid was dried under high vacuum and obtained in a 65.4% yield.

TABLE 1

Reduction in Viral Titer at Different Concentrations of B
($Log_{10}$ Reduction)

| UVA Fluence ($J/cm^2$) | 50 µg/mL | 100 µg/mL | 200 µg/mL | 300 µg/mL | 400 µg/mL |
|---|---|---|---|---|---|
| 4.32  | 0.50 | 0.75 | 1.50 | 1.0  | 0.75 |
| 12.96 | 1.33 | 2.25 | 3.25 | 3.25 | 4.0  |
| 25.92 | 1.50 | 2.50 | 5.25 | 5.25 | 5.25 |
| 51.84 | 4.67 | 6.50 | 7.0  | 7.0  | ND   |

Abbreviation: ND, Not Determined

TABLE 2

Evaluation of mouse fibroblast cells following 72 hour incubation after exposure to non-UVA irradiated solutions of B  N = Indicates a negative or nontoxic response; I = Indicates an intermediate response, a subjective assessment of the extent of cellular response; T = Indicates a positive or toxic response consisting of greater than 50% cell death.

| Samples | Confluent Monolayer | Vacuolization | Swelling | Crenation | % Lysis | CTE Score |
|---|---|---|---|---|---|---|
| 600 µg/mL   | + | + | − | − | 0 | N |
| 300 µg/mL   | + | − | − | − | 0 | N |
| 150 µg/mL   | + | − | − | − | 0 | N |
| 75 µg/mL    | + | − | − | − | 0 | N |
| 37.5 µg/mL  | + | − | − | − | 0 | N |
| Control (−) | + | − | − | − | 0 | N |

CTE = Cytotoxic Effects Score
N = Nontoxic

TABLE 3

Viability of AE-1 cells and CHO cells in calf sera that had been pretreated with 30 µg/mL of B at different UVA fluences.

| Treatment | CP38 µg/mL | Mean Viable AE-1 Cells ($\times 10^5$/mL) | | | | Mean Viable CHO Cells ($\times 10^5$/mL) | | |
|---|---|---|---|---|---|---|---|---|
|   |   | Day 2 | Day 5 | Day 7 | Mean ± sd | Day 4 | Day 7 | Average |
| Control      | 0  | 1.83 | 2.63 | 3.09 | 2.52 ± 0.64 | 10.5 | 0.87 | 5.69 |
| 0 J/cm$^2$   | 30 | 1.80 | 2.24 | 3.02 | 2.35 ± 0.62 | 12.9 | 3.3  | 8.10 |
| 4.2 J/cm$^2$ | 30 | 1.99 | 2.06 | 3.00 | 2.35 ± 0.56 | 12.4 | 2.6  | 7.50 |
| 8.4 J/cm$^2$ | 30 | 1.75 | 2.00 | 2.60 | 2.12 ± 0.44 | 10.7 | 2.0  | 6.35 |
| 16.8 J/cm$^2$| 30 | 1.67 | 2.32 | 2.63 | 2.21 ± 0.49 | 11.3 | 0.62 | 5.96 |
| 25.2 J/cm$^2$| 30 | 1.78 | 2.99 | 4.10 | 2.96 ± 1.16 | 13.0 | 2.2  | 7.6  |

TABLE 4

Viability of AE-1 cells and CHO cells in calf sera that had been pretreated with different concentrations of B

| Treatment | Mean Viable AE-1 Cells ($\times 10^5$/mL) | | | | Mean Viable AE-1 Cells ($\times 10^5$/mL) | | | |
|---|---|---|---|---|---|---|---|---|
|   | Day 2 | Day 4 | Day 7 | Mean ± sd | Day 4 | Day 7 | Day 11 | Mean ± sd |
| Control    | 0.77 | 1.6 | 6.1 | 2.82 ± 2.86 | 27.2 | 17.5 | 19.9 | 21.5 ± 5.1  |
| 60 µg/mL   | 1.0  | 3.1 | 4.7 | 2.93 ± 1.86 | 35.4 | 16.6 | 14.0 | 22.0 ± 11.7 |
| 90 µg/mL   | 1.1  | 3.3 | 4.6 | 3.00 ± 1.77 | 32.4 | 20.1 | 15.1 | 22.5 ± 8.9  |
| 120 µg/mL  | 1.1  | 2.6 | 4.7 | 2.80 ± 1.81 | 34.5 | 19.5 | 14.4 | 22.8 ± 10.4 |
| 150 µg/mL  | 1.1  | 2.3 | 4.7 | 2.70 ± 1.83 | 33.3 | 16.3 | 11.0 | 20.2 ± 11.7 |

TABLE 5

Selective Binding Properties of Photosensitizers

| Compound | % Above Equilibrium Concentration | | Ratio*: | |
| --- | --- | --- | --- | --- |
| | % Lipid | % DNA | Lipid/DNA | N |
| B | 7.2 ± 1.8 | 11.2 ± 3.5 | 0.7 | 5 |
| A | 0 | 8.5 ± 1.1 | 0 | 3 |
| C | 0 | 20.6 ± 7.6 | 0 | 3 |
| AMT | 11.6 ± 0.7 | 3.4 ± 2.9 | 3.4 | 3 |
| Khellin | 3.2 ± 0.3 | 1.8 ± 0.2 | 1.8 | 3 |
| Visnagin | 2.7 ± 0.8 | 5.0 ± 1.3 | 0.5 | 3 |
| Methylene Blue | 0.0 ± 0 | 19.7 ± 1.5 | 0 | 3 |
| Ethidium Bromide | 1.0 ± 0.5 | 25.8 ± 0.9 | 0.04 | 3 |
| Proflavine | 7.1 ± 2.4 | 16.2 ± 1.0 | 0.4 | 3 |

\* >1, Lipid preference
<1, DNA preference
1, No preference

TABLE 6

Summary of platelet in vitro properties following photoinactivation using B (300 µg/mL) and UVA light (25 J/cm$^2$)

| Assay | Day 0* | | Day 3* | | Day 4* | |
| --- | --- | --- | --- | --- | --- | --- |
| | Control | Treated | Control | Treated | Control | Treated |
| HSR | 65 ± 10 | 50 ± 7 | 70 ± 8 | 38 ± 22 | 64 ± 12 | 0 |
| % Control | | 78 ± 12 | | 47 ± 22 | | 0 |
| Morphology | 308 ± 27 | 300 ± 27 | 288 ± 27 | 232 ± 24 | 280 ± 40 | 203 ± 7 |
| % Control | | 94 ± 5 | | 81 ± 10 | | 74 ± 10 |
| pH | 7.41 ± 0.10 | 7.29 ± 0.08 | 7.34 ± 0.18 | 6.37 ± 0.25 | 7.18 ± 0.33 | 5.84 ± 0.19 |
| N | 14 | 14 | 12 | 12 | 5 | 5 |
| Post-UV treatment addition of 20 mM bicarbonate (final concentration): | | | | | | |
| HSR | 56 ± 9 | 46 ± 2 | 64 ± 7 | 41 ± 10 | 57 ± 9 | 50 ± 18 |
| % Control | | 97 ± 3 | | 64 ± 8 | | 86 ± 19 |
| Morphology | 323 ± 4 | 277 ± 22 | 288 ± 20 | 257 ± 14 | 293 ± 41 | 274 ± 31 |
| % Control | | 92 ± 6 | | 90 ± 10 | | 94 ± 7 |
| pH | 7.32 ± 0.04 | 7.23 ± 0.05 | 7.30 ± 0.07 | 7.31 ± 0.04 | 7.26 ± 0.11 | 7.05 ± 0.14 |
| N | 3 | 3 | 3 | 3 | 3 | 3 |

HSR, hypotonic shock response
*Post-treatment storage (platelets were 24 hours old at Day 0)
Random donor platelet concentrates were pooled and subsequently divided into control and treated units. Photoinactivation was carried out in CLX containers containing 50 mL platelet concentrates and 10 mL of sensitizer solution in 0.9% saline (CP-38, 1.8 mg/mL). 2 mL of 5% sodium bicarbonate solution (20 mM final concentration in platelet concentrates) was added following photoinactivation treatment.

TABLE 7

Summary of pheresed platelet in vitro properties following photoinactivation using B (300 µg/mL) and UVA light (25 J/cm$^2$)

| Assay | Day 0* | | Day 3* | | Day 4* | |
| --- | --- | --- | --- | --- | --- | --- |
| | Control | Treated | Control | Treated | Control | Treated |
| Hypotonic shock response (HSR) | 77 ± 6 | 69 ± 9 | 76 ± 3 | 71 ± 6 | 75 ± 7 | 42 ± 28 |
| % Control | | 88 ± 3 | | 93 ± 8 | | 55 ± 34 |
| Morphology score | 335 ± 15 | 333 ± 12 | 293 ± 31 | 273 ± 20 | 305 ± 15 | 208 ± 40 |
| % Control | | 97 ± 4 | | 92 ± 10 | | 68 ± 13 |

TABLE 7-continued

Summary of pheresed platelet in vitro properties following photoinactivation using B (300 μg/mL) and UVA light (25 J/cm²)

| | Day 0* | | Day 3* | | Day 4* | |
|---|---|---|---|---|---|---|
| Assay | Control | Treated | Control | Treated | Control | Treated |
| Collagen aggregation | 79 ± 6 | 67 ± 6 | 71 ± 7 | 61 ± 14 | 71 ± 9 | 41 ± 23 |
| % of control | | 86 ± 4 | | 86 ± 18 | | 58 ± 32 |
| GMP-140 expression | 11 ± 5 | 10 ± 4 | 14 ± 7 | 30 ± 18 | 22 ± 6 | 68 ± 17 |
| pH | 7.50 ± 0.05 | 7.36 ± 0.06 | 7.47 ± 0.05 | 6.73 ± 0.13 | 7.45 ± 0.03 | 6.09 ± 0.20 |
| N | 9 | 9 | 9 | 9 | 6 | 6 |

*Post-treatment storage (platelets were 24 hours old at Day 0)
Pheresed platelet concentrates were divided into control and treated units.
Photoinactivation was carried out in PL 732 containers containing 50 mL platelet concentrates and 10 mL of sensitizer solution in 0.9% saline (B 1.8 mg/mL). HSR, hypotonic shock response.

TABLE 8

Summary of platelet in vitro properties following photoinactivation using A (200 μg/mL) and UVA light (29 J/cm²)

| | Day 1 | | Day 4 | | Day 5 | |
|---|---|---|---|---|---|---|
| Assay | Control | Treated | Control | Treated | Control | Treated |
| Cell Count (×10¹¹) | 0.73 ± 0.2 | 0.63 ± 0.25 | 0.71 ± 0.24 | 0.74 ± 0.2 | 0.71 ± 0.21 | 0.78 ± 0.21 |
| Morphology Score | 302 ± 25 | 251 ± 16 | 267 ± 26 | 238 ± 15 | 257 ± 36 | 226 ± 21 |
| % Discs | 57 ± 12 | 36 ± 8 | 46 ± 10 | 30 ± 8 | 41 ± 16 | 23 ± 9 |
| HSR (%) | 62 ± 9 | 46 ± 7 | 72 ± 4 | 52 ± 7 | 74 ± 6 | 48 ± 7 |
| pH at room temp. | 7.37 ± 0.09 | 7.20 ± 0.05 | 7.38 ± 0.16 | 6.96 ± 0.16 | 7.37 ± 0.18 | 6.69 ± 0.22 |
| Lactate (m mole/L) | 5.6 ± 1.2 | 5 ± 1 | 16 ± 4 | 16 ± 2 | 15 ± 3 | 18 ± 2 |
| pO2 (mm Hg) | 87 ± 35 | 59 ± 47 | 113 ± 18 | 135 ± 14 | 53 ± 30 | 33 ± 14 |
| PCO2 (mm Hg) | 30 ± 5 | 37 ± 7 | 16 ± 2 | 13 ± 3 | 17 ± 2 | 20 ± 7 |
| Aggreg. Rate | 39 ± 6 | 21 ± 7 | 35 ± 8 | 21 ± 6 | 34 ± 7 | 18 ± 6 |
| Aggreg. Extent | 48 ± 5 | 35 ± 8 | 45 ± 10 | 34 ± 7 | 43 ± 9 | 31 ± 9 |
| GMP-140 expression (%) | 35 ± 16 | 38 ± 14 | 31 ± 10 | 51 ± 11 | 42 ± 11 | 67 ± 9 |
| N | 6 | 6 | 6 | 6 | 6 | 6 |

One day old random donor platelet concentrates in CLX containers were subjected to photoinactivation under specified conditions in a prototype UVA reactor. Platelet in vitro properties were measured after treatment and subsequent storage in a platelet incubator with constant agitation.
Aggregation response was measured with dual agonist ADP (80 μM) and Collagen (8 μg/mL) in an aggregometer.

We claim:

1. A photosensitizer capable of binding viral, bacterial, or parasitic contaminants in a biological solution, and further capable of inactivating said viral, bacterial or parasitic contaminant upon irradiation without substantially impairing said biological solution, comprised of the formula:

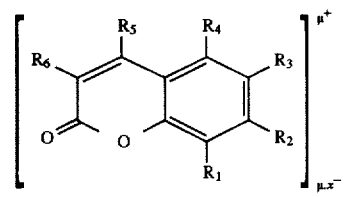

wherein μ is an integer of 1 ; X is an anionic counterion; Z is N or P; $R_1$, $R_2$, $R_3$, $R_4$, $R_5$, and $R_6$ are independently halo; H; linear or branched alkyl of 1–10 carbon atoms; liner or branched alkoxy of 1–10 carbon atoms; $(CH_2)_mO(CH_2)_pZ\oplus R'R''R'''$ or $—O(CH_2)_nZ\oplus R'R''R'''$ wherein n, m and p are independently integers from 1 to 10 and R',R", and R'" are independently H or linear or branched alkyl of 1 to 10 carbon atoms with the proviso that on each Z atom, not more than two of R',R", or R'"may by H; and at least on one of $R_1$, $R_2$, $R_3$, $R_4$, $R_5$ or $R_6$ is $—(CH_2)_mO(CH_2)_pZ\oplus R'R''R'''$ or $—O(CH_2)_nZ\oplus R'R''R'''$.

2. The photosensitizer of claim 1 wherein $R_6$ is selected from the group consisting of F, Cl, Br, and I.

3. The photosensitizer of claim 2 wherein $R_6$ is Br.

4. The photosensitizer of claim 2 wherein $R_6$ is Cl.

5. The photosensitizer of claim 1 wherein $R_2$ is $OCH_2CH_2CH_2N\oplus(CH_2CH_3)_3$ $Br^-$.

6. The photosensitizer of claim 1 wherein $R_1$ is $CH_3$ or H.

7. The photosensitizer of claim 1 having the formula:

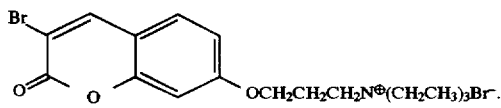

8. The photosensitizer of claim 1 having the formula:

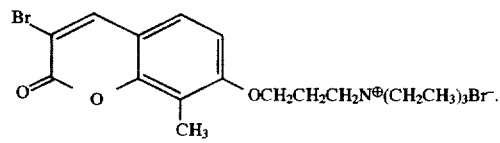

9. The photosensitizer of claim 1 having the formula:

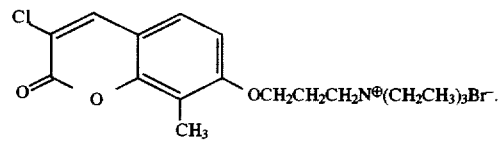

10. The photosensitizer of claim 1 having the formula:

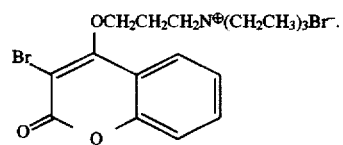

11. A photosensitizer according to any one of claims 1–7 wherein one of $R_1$, $R_2$, $R_3$, $R_4$, $R_5$ or $R_6$ is $(CH_2)_mO(CH_2)_pZ\oplus R'R''R'''$ or $—O(CH_2)_nZ\oplus R'R''R'''$.

* * * * *